US012721562B2

(12) United States Patent
Viana et al.

(10) Patent No.: US 12,721,562 B2
(45) Date of Patent: Sep. 1, 2026

(54) ELECTROCHEMICALLY ACTIVATED AND REDUCED GRAPHENE OXIDE STRUCTURE

(71) Applicants: FUNDACIÓ INSTITUT CATALÀ DE NANOCIÈNCIA I NANOTECNOLOGIA (ICN2), Barcelona (ES); INSTITUCIÓ CATALANA DE RECERCA I ESTUDIS AVANÇATS (ICREA), Barcelona (ES)

(72) Inventors: Damià Viana, Barcelona (ES); José Garrido, San Just Desvern (ES); Steven Waltson, Los Angeles, CA (US)

(73) Assignees: FUNDACIÓ INSTITUT CATALÀ DE NANOCIENCIA I NANOTECNOLOGIA (ICN2), Barcelona (ES); INSTITUCIÓ CATALANA DE RECERCA I ESTUDIS AVANATS (ICREA), Barcelona (ES)

(*) Notice: Subject to any disclaimer, the term of this patent is extended or adjusted under 35 U.S.C. 154(b) by 274 days.

(21) Appl. No.: 18/566,540

(22) PCT Filed: May 31, 2022

(86) PCT No.: PCT/EP2022/064744
§ 371 (c)(1),
(2) Date: Dec. 1, 2023

(87) PCT Pub. No.: WO2022/253827
PCT Pub. Date: Dec. 8, 2022

(65) Prior Publication Data

US 2024/0268740 A1 Aug. 15, 2024

(30) Foreign Application Priority Data

Jun. 3, 2021 (EP) .................................... 21382496

(51) Int. Cl.
*A61B 5/263* (2021.01)
*A61N 1/05* (2006.01)
*C25B 3/07* (2021.01)

(52) U.S. Cl.
CPC ............ *A61B 5/263* (2021.01); *A61N 1/0534* (2013.01); *A61N 1/0551* (2013.01); *C25B 3/07* (2021.01); *A61B 2562/125* (2013.01)

(58) Field of Classification Search
CPC ......... A61B 5/263; A61B 5/291; A61B 5/369; A61B 5/4064; A61B 5/4094;
(Continued)

(56) References Cited

U.S. PATENT DOCUMENTS

2017/0352869 A1 12/2017 Zhamu et al.

FOREIGN PATENT DOCUMENTS

| | | | | |
|---|---|---|---|---|
| CN | 108404689 A | * | 8/2018 | C02F 1/44 |
| CN | 111604061 A | * | 9/2020 | C25B 1/02 |
| GB | 2585828 A | * | 1/2021 | A61B 5/05 |

OTHER PUBLICATIONS

Huang et al. Structural Evolution of Hydrothermally Derived Reduced Graphene Oxide, 2018, Scientific Reports, 8:6849, DOI: 10.1038/s41598-018-25194-1 (Year: 2018).*
(Continued)

*Primary Examiner* — Eun Hwa Kim
(74) *Attorney, Agent, or Firm* — McCoy Russell LLP

(57) ABSTRACT

The present invention relates to a reduced graphene oxide structure for stimulation and/or recording of the central and/or peripheral nervous system comprising a stack of layered, reduced graphene oxide flakes, wherein the reduced graphene oxide structure is electrochemically activated.

14 Claims, 43 Drawing Sheets

(58) Field of Classification Search
CPC .. A61B 5/4836; A61N 1/0534; A61N 1/0551; A61N 1/00529; A61N 1/36064; A61N 1/36067; A61N 1/36071
See application file for complete search history.

(56) References Cited

OTHER PUBLICATIONS

Eda, G. et al., "Chemically derived graphene oxide: towards large-area thin-film electronics and optoelectronics," Advanced Materials, vol. 22, No. 22, Jun. 11, 2010, 24 pages.
Chen, H. et al., "Reduction of free-standing graphene oxide papers by a hydrothermal process at the solid/gas interface," RCS Advances, vol. 3, No. 9, Dec. 21, 2012, 8 pages.
Apollo, N. et al., "Soft, Flexible Freestanding Neural Stimulation and Recording Electrodes Fabricated from Reduced Graphene Oxide," Advanced Functional Materials, vol. 25, No. 23, Jun. 17, 2015, 9 pages.
Bramini, M. et al., "Interfacing Graphene-Based Materials With Neural Cells," Frontiers in Systems Neuroscience, Apr. 11, 2018, 42 pages.
Liu, D. et al., "Electrolyte-assisted hydrothermal synthesis of holey graphene films for all-solid-state supercapacitors," Journal of Materials Chemistry A, vol. 6, No. 24, May 16, 2018, 10 pages.
ISA European Patent Office, International Search Report and Written Opinion Issued in Application No. PCT/EP2022/064744, Aug. 17, 2022, WIPO, 11 pages.

* cited by examiner a b

ELECTROCHEMICALLY ACTIVATED AND REDUCED GRAPHENE OXIDE STRUCTURE

CROSS REFERENCE TO RELATED APPLICATIONS

The present application is a U.S. National Phase of International Application No. PCT/EP2022/064744 entitled "AN ELECTROCHEMICALLY ACTIVATED AND REDUCED GRAPHENE OXIDE STRUCTURE," and filed on May 31, 2022. International Application No. PCT/EP2022/064744 claims priority to European Patent Application No. 21382496.4 filed on Jun. 3, 2021. The entire contents of each of the above-listed applications are hereby incorporated by reference for all purposes.

TECHNICAL FIELD

The present invention relates to a reduced graphene oxide structure for stimulation and/or recording of the central and/or peripheral nervous system, and to a method for preparing an electrochemically activated and reduced graphene oxide structure. The present invention further relates to an electrode device comprising the reduced graphene oxide structure.

BACKGROUND AND SUMMARY

In practice, it is known that stimulation and/or recording of the central and/or peripheral nervous system is a method for the diagnosis and therapy of neurodegenerative diseases such as inter alia the Parkinson's disease, epilepsy, and chronic pain. In this respect, electrical stimulation by means of leads which were implanted into brain areas or regions like the subthalamic nucleus and/or the globus pallidus internus can e.g. alleviate the tremor symptoms of a patient suffering from a drug-resistant Parkinson's disease. Further, the signals from a brain region or area at which the leads were implanted can be recorded and the condition and/or constitution of the brain tissue can be determined using impedance measurements.

In this relation, neuroprosthetic devices are powerful tools to monitor, prevent and treat neural diseases, disorders and conditions by interfacing electrically with the nervous system. They are capable of recording and stimulating electrically neural activity once implanted in the nervous tissue. Currently, most neuroprosthetic technologies base their interface with the neural tissue on electrodes. The interfacing can occur through Faradaic or capacitive currents. One the one hand side, Faradaic currents are associated to redox reactions taking place in the electrode/tissue interface. Those reactions can end up potentially degrading the electrode and damaging the tissue. On the other hand, capacitive currents are due to the charge and discharge of the double layer that appears when an electrical conductor is placed in a liquid environment.

For implants, capacitive currents are always preferred over the Faradaic ones since they do not harm the tissue nor degrade the electrode material. Thus, high capacitances are ideal to achieve effective and safe interfacing with the neural tissue. The capacitance sets performance values such as the charge injection limit (CIL) of the material and its impedance. High levels of charge injection and low impedances are desired when recording and stimulating the neural activity of the nervous system.

The size of electrodes is limited by the performance of the materials they are made of; materials with high performance, in terms of high capacitance, allow higher levels of miniaturization.

Interface precision and device durability, however, are aspects to be improved in order to increase the acceptance of the technology, improve its therapeutic application, and reduce post-operatory complications. The interface precision can be improved by reducing electrodes sizes and increasing the resolution of electrode arrays. Typically, electrodes exhibit miniaturization limitations due to the intrinsic impedance and charge injection limit of the materials they are made of. Additionally, the durability of a device partially depends on the chemical stability of the electrode's material and to some extent on its biocompatibility (including its stability to tissue response) and/or its biodegradability. In turn, the mechanical compliance with the living tissue should be considered to avoid any damage of the affected tissue due to too great a difference in stiffness.

The immune response of the body to the materials is another factor to take into account when implanting devices in living tissue. For example, scar tissue formation and inflammation around the implant area can occur. The immune response tends to encapsulate foreign bodies, which decrease the electrical performance of the device over time. Those materials possessing a strong stiffness mismatch with the tissue where are implanted are more aggressively attacked by the body. Therefore, flexible and soft materials are desired over rigid or thick ones. Thin devices are also necessary to minimize the immune response.

Long term stability of the material is also a crucial aspect to consider for chronic implants, being required materials with high chemical and mechanical stabilities.

Standard commercially available neural interfaces are based on metallic microelectrodes made of platinum Pt, platinum-iridium (Pt/Ir), iridium oxide (IrOx) or titanium nitride (TiN). Those materials interact with the living tissue through a combination of Faradaic and capacitive currents, offer a limited chemical stability and are rigid. Metals performance strongly drops in microelectrodes of tens of micrometres in diameter; further, metals degrade over continuous tissue stimulation.

Recently, conductive polymers, such as the polymer mixture poly(3,4-ethylenedioxythiophene) polystyrene sulfonate (PEDOT:PSS), have emerged as promising candidates to overcome metallic microelectrodes limitations. However, when implanted, its interface with the tissue is also through a combination of Faradaic and capacitive currents. By improving the impedance and CIL of metals, together with their flexibility, higher performance in the recording and stimulation of neural tissue can be achieved. However, delamination can occur, thereby compromising the long-term stability. It has been described that PEDOT:PSS has problems during the stimulation since it degrades chemically and mechanically when is under operation.

Graphene is a material with very promising properties for neural interfacing. Being electrically conductive, flexible, mechanically robust and highly inert, it is a good candidate for safe electrical interfacing in aqueous environments. The performance of single layer graphene microelectrodes, however, is far from being optimal for neural interfacing, in particular for applications requiring stimulation of the neural tissue. As the impedance is limited by the capacitance of the graphene/tissue interface and the stimulation is a capacitive process, three-dimensional porous graphene-based materials with large area to volume ratios have been suggested to overcome this issue. However, it has been reported that such graphene materials processed from flakes including the porous graphene-based materials reported to date, including those ones made of reduced graphene oxide, require thicknesses in the range of hundreds of micrometers to achieve valid properties for the stimulation.

From M. Chhowalla et al., "Chemically Derived Graphen Oxide: Towards Large-Area Thin-Film Electronics and Optoelectronics", Adv. Mater., 2010, 22, 2393-2415, it is known that chemically derived graphene possesses a unique set of properties arising from oxygen functional groups that are introduced during chemical exfoliation of graphite. Large-area thin-film deposition of graphene oxide (GO), enabled by its solubility in a variety of solvents, offers a route towards GO-based thin-film electronics and optoelectronics. The electrical and optical properties of GO are strongly dependent on its chemical and atomic structure and are tunable over a wide range via chemical engineering. As-synthesized GO films are typically insulating, exhibiting sheet resistance value of about $10^{12}\Omega\ sq^{-1}$ or higher. The insulating nature of GO is attributed to the absence of percolating pathways among $sp^2$ carbon clusters to allow classical carrier transport to occur. However, reduction of GO results in decrease in resistance by several orders of magnitude.

Thus, by reducing GO its electrical conductivity can be initiated and adjusted.

It is further known from H. Lin et al., "Reduction of free-standing graphene oxide papers by a hydrothermal process at the solid/gas interface", RSC Adv. 2013, 3, 2971-2978, that hydrothermal reduction of graphene oxide where oxygen functional groups such as carbonyls and epoxides were effectively removed results in relatively high electrical conductivity, wherein the resulting conductivity is dependent on the hydrothermal temperature, the reducing time and the concentration of ammonia which was added to the reduction process performed by H. Lin et al.

Hence, hydrothermal reduction of GO appears to be the most promising approach to optimize the electrical properties of this material. A further improvement of the properties might be achieved by the addition of ammonia to the reduction process.

In H. Zhao et al., "Electrolyte-assisted hydrothermal synthesis of holey graphene films for all-solid-state supercapacitors", J. Mater. Chem. A., 2018, 6, 11471-11478, it has been shown that after hydrothermal treatment, the reduced holey graphene films (rHGFs) maintained their flexibility, integrity and porosity, which resulted from the electrolyte-induced balance between electrostatic repulsion and π-π attraction. The trapped electrolyte ($H_2SO_4$) between graphene layers can prevent aggregation, and the resulting supercapacitor exhibits a high specific capacitance in the sulfuric acid electrolyte. Benefitting from the in-plane pores and oxygen containing groups on graphene sheets, the rHGF electrode exhibits a high specific capacitance of 260 $F\ g^{-1}$ with remarkable rate performance in a three-electrode system.

Accordingly, the capacitive properties of reduced graphene can be increased by trapped electrolyte between the graphene layers.

On this basis, the ideal material to be used as a neural electrode should satisfy the following requirements. It must be biocompatible, so it should not induce a toxic or necrotic response to the adjacent tissue, nor an excessive foreign body or immune response. The material must maintain its integrity during the implantation period. In case of chronic use, the electrodes should be embedded into flexible devices to withstand small displacements between the tissue and the device after the implantation. The electrode/tissue interface should permit the electrical activity from the tissue to be recorded with high signal-to-noise ratio and that sufficient charge can be injected to it in order to elicit action potentials. Also, the electrode dimensions must accommodate to the morphology of the target nervous tissue, so it can adapt itself to it and convey in an accurate way naturalistic electrical pattern. During electrical stimulation, Faradaic reactions should be avoided to prevent toxicity to the surrounding tissue and electrode corrosion which might lead to premature failure of the interface. Instead, capacitive currents are advised. Finally, the electrical features of the electrode material, such as the impedance and the CIL, should not degrade during the life-time of the implant.

It is an object of the present invention to provide a reduced graphene oxide structure for stimulation and/or recording of the central and/or peripheral nervous system, a method for preparing an electrochemically activated and reduced graphene oxide structure and also an electrode device comprising the reduced graphene oxide structure, especially such that a reduced graphene oxide structure is obtained, which provides the requirements of the aforementioned kind, in particular in such a way that the capacitance of the structure is increased while the impedance is low.

This object is solved by a reduced graphene oxide structure for stimulation and/or recording of the central and/or peripheral nervous system with the features claim 1. Accordingly, a reduced graphene oxide structure for stimulation and/or recording of the central and/or peripheral nervous system is provided, which comprises a stack of layered reduced graphene oxide flakes, wherein the reduced graphene oxide structure is electrochemically activated.

The basic idea of the present invention is to increase the electrochemically available surface area (EASA) by electrochemically activating the structure. The electrochemical activation is inter alia done in an electrolyte solution, in particular by causing charged ions to permeate into the structure. Thereby, not only the outer surfaces of the structures are electrochemically available and subject to the electrochemical activation, but the interfaces between the layers as well. As a result, the capacitance of the structure is significantly increased. Also, the impedance can be kept on a low level.

The obtained structure permits to stimulate a nervous system with high charge densities over millions of pulses when implemented into microelectrodes of cellular dimensions, wherein the structure itself is thin and flexible such that it can adapt to the morphology and anatomy of the brain tissue without becoming mechanically instable or delaminating. Moreover, the structure is biocompatible and does not experiment any degradation.

For the purposes of the invention, the term "graphene oxide" (GO) refers to a material comprising carbon atoms like graphene but also comprising a population or quantity of oxygen functional groups. The term "reduced graphene oxide" (rGO) refers to graphene oxide (GO) that has been reduced by a reduction process, such as for example a hydrothermal reduction process, and as a consequence has a reduced oxygen content in comparison to the GO before the reduction step (i.e. non-reduced GO). The term "HTrGO" refers to hydrothermally reduced graphene oxide (GO).

The reduced graphene oxide structure forming the starting material for the electrochemical activation can inter alia be prepared by the following steps:

a) filtering a graphene oxide solution through a porous membrane thereby forming a GO structure on the membrane top, wherein in particular the GO solution is and aqueous solution, the concentration of GO in the solution is from 0.001 to 5 mg/mL, and the volume filtered is from 5 to 1000 mL;

b) transferring the GO structure from the membrane onto a sacrificial substrate, whereby the GO structure is placed between the membrane at the top and the sacrificial substrate at the bottom;

c) removing the membrane, whereby the GO structure remains attached onto the sacrificial substrate;

d) hydrothermally reducing the GO structure to form a reduced GO structure, in particular at a temperature from 100 to 240° C., under a pressure from $10^5$ to $4 \cdot 10^8$ Pa, for a time period from 1 min to 24 h, and in the presence of water; and e) detaching the rGO structure from the sacrificial substrate.

The GO structure contains a high degree of defects and is electrically insulating. In the hydrothermal reduction, the structure is exposed to subcritical water. During this process, the protons from the water react with the oxygen-containing functionalizations of the flakes, partially removing them and opening in-plane holes or pores. Contrary to chemically or just thermally reduction, this process permits the structure to be permeable to aqueous solutions while being electrically conductive. The synthesis of the structure does not involve any hazardous chemical, so the structure biocompatibility is maintained.

The term "charge storage capacitance (CSC)" as used herein refers to the maximal amount of charge that a system consisting of two electrically conductive media separated by a dielectric medium can withstand at a given potential difference. To obtain the charge storage capacitance of a system, cyclic voltammetry technique can be performed. For that, the voltage applied to it is varied cyclically and the current measured. The accumulated charge due to the measured current corresponds to the charge storage capacitance. The charge storage capacitance is measured in coulombs (C). Accordingly, the term "cathodic CSC (cCSC)" as used herein refers to the charge stored during the negative phase of the current, is usually used as a figure of merit to determine the performance of electrodes.

The term "charge injection limit (CIL)" as used herein refers to the maximal amount of charge that can be injected to the electrolyte media through an electrode without inducing irreversible faradaic reactions. Ideally, the charge is injected only through capacitive currents and avoids reversible faradaic reactions. The charge injection limit is measured in $mC/cm^2$.

The term "capacitance" refers to the ratio between the charge stored in the capacitor and the given potential difference. The capacitance is measured in Farads (F).

The term "impedance" as used herein refers to the measure of the opposition that a circuit presents to a current when a voltage is applied. The impedance of an electric circuit can be obtained dividing the current flowing through it by the voltage signal applied. The impedance is measured in Ohms (Ω). According to the behaviour of the current and the voltage, a capacitance can be identified and fitted to the impedance. When referred to electrodes, the impedance is called interfacial impedance.

The term "stability" of the rGO film as used herein is understood as no increase of the interfacial impedance over continuous electrical pulsing for at least 100 million pulses.

In a possible embodiment, the rGO structure is obtainable by hydrothermal reduction, as described above in step d).

In a further possible embodiment, the rGO structure is obtainable by electrochemically activation in an electrolyte system, preferably an aqueous environment.

The electrolyte system provides charged ions during cyclic voltammetry to increase the CSC of the structure, since the charged ions immerse into the structure and thereby extending the EASA.

In another possible embodiment, the rGO structure comprises a plurality of holes having a diameter equal to or less than 10 nm.

The holes permit charged ions to permeate or enter into the structure, in particular into the interlayer planes.

In a further possible embodiment, the holes are permeable for charged ions.

Accordingly, the charged ions can permeate or enter the structure and arrange themselves between the layered rGO flakes of the structure.

In yet another possible embodiment, the charged ions are arranged between the layers of the structure and on the outer surfaces of the structure.

It is known that due to cyclic voltammetry in a solution charged ions accumulate on the surface of a structure through electrosorption mechanisms leading to capacitive and Faradaic currents. Within a certain potential window, no Faradaic reactions are observed and the current is due to capacitive interactions. As mentioned above, due to the holes which are formed during hydrothermal reduction the charged ions can also immerse into the structure, such that not only the outer surfaces of the structure are electrically available but the interfaces within the structure as well.

In a further possible embodiment, the distance between two consecutive layers of the rGO structure is between 0.2 nm and 0.7 nm, preferably between 0.3 nm and 0.5 nm.

After the reduction step, the structure lost half of its height, because of the decrease to the half of the interstacking flakes distance. The oxygen functionalities of the GO flakes set a limit to the distance the flakes can come close together, but when partially removed during hydrothermal reduction, the flakes can stack tighter. In case of a hydrothermal reduction at 134° C. for 3 hours, interlayer distances of about 0.4 nm can be measured.

In a further possible embodiment, the thickness of the reduced graphene oxide structure is between 20 nm to 5 μm, preferably between 500 nm to 4000 nm.

Thereby the structure is sufficiently thin and flexible but without losing its stability.

The object of the present invention can further by solved by a method for preparing an electrochemically activated and reduced graphene oxide structure, which comprises the following steps:

providing graphene oxide structure comprising a stack of layered graphene oxide flakes;

reducing the graphene oxide structure; and electrochemically activating the rGO structure in an electrolyte system, preferably an aqueous environment, wherein electrochemically activating comprises at least partially sweeping cyclically an electrical potential around a potential equilibrium within a plurality of predetermined ranges.

This has the advantage that the electrical conductivity and capacitance is improved, while lowering the impedance. Within appropriate limits, this method can be applied with no irreversible damage like Faradaic reactions of the structure until being able to inject up to 10 $mC/cm^2$, depending on the thickness and size of the structure.

Upon sweeping or shifting the potential around the equilibrium, charged ions of the electrolyte system can permeate through holes formed by the hydrothermal reduction into the bulk structure, thereby increasing the EASA and accordingly the capacitance.

In a possible embodiment, the graphene oxide structure is reduced hydrothermally.

In another possible embodiment, the ranges are predetermined such that Faradaic reactions being avoided.

Accordingly, no net transfer of electrons between the electrode and the electrolyte is implied, causing the reduction or oxidation of chemical species of the electrolyte. Faradaic reactions take place at the interface between the structure and the electrolyte, causing the structure to undergo a degradation and leading to the generation of subproducts that could damage the brain tissue when the structure is used in a neural electrode.

In a further possible embodiment, electrochemically activating comprises charged ions permeating into the rGO structure, thereby preferably losing their solvation shell.

As already explained above, charged ions within the structure increase the EASA and thus the capacitance, wherein the loss of the solvation shells additionally increases the capacitance.

In yet another possible embodiment, the predetermined ranges are consecutive, wherein each succeeding range is equal to or greater than its preceding range.

By a stepwise increase of the ranges, the cCSC can be increased until a certain saturation level is reached in the respective range without Faradaic reactions affecting the structure. The saturation level can be either defined by a specific cCSC value which will not be reached within a reasonable period or by a specific gradient indicating the change rate of the cCSC.

In a further possible embodiment, the number of sweeping cycles within each succeeding range is equal to or greater than the number of sweeping cycles within its preceding range.

Experiments have shown that the greater the range within which the cyclic voltammetry is performed the more cycles are required to reach a certain saturation level, i.e. no significant improvement is achievable so far. Nevertheless, the increase of performance of the structure, e.g. the increase of the cCSC, occurs substantially within the first cycles of the respective range.

The object of the present invention can further by solved by an electrode device for stimulation and/or recording of the central and/or peripheral nervous system, preferably for neurostimulation and recording, wherein the electrode comprises the rGO structure as defined above.

The term "electrode" as used herein refers to an electrical conductor that interfaces two media. In this case, it connects the body (or tissue from the body) to a device for eliciting electrical signals (e.g. for providing neural stimulation) and/or receiving electrical signals (e.g. for monitoring neural activity), i.e. preferably a bidirectional electrode.

An electrode comprising the rGO structure defined above provides a performance, in particular a capacitance, some orders of magnitude higher upon electrochemically activating by cyclic voltammetry, i.e. by sweeping the electrical potential around the equilibrium, than without activation, depending on the number and width of the determined ranges as well as the number of cycles within each range.

In another possible embodiment, the rGO structure has a diameter of 25 μm or less and provides a charge injection limit from 2 $mC/cm^2$ to 10 $mC/cm^2$ and/or an impedance of 10 to 100 kΩ at a frequency of 1 kHz in an electrolyte system.

As a result of the treatment steps hydrothermally reduction and electrochemical activation microelectrodes can be manufactured which outperform established microelectrode made of Pt, TiN or the like by at least one magnitude, referred to the capacitance, wherein the rGO-based microelectrode is proven to be biocompatible and stable.

The given values of the CIL and the impedance are the results of conducted experiments. However, this does not exclude the possibility that, for example, by adding ammonium to the hydrothermal reduction and the electrolyte system, the performance of the microelectrodes can be increased even further.

In the following, further advantages and embodiments of the present invention are described in conjunction with the attached drawings. Thereby, the expression "left", "right", "below", and "above" are referred to the drawings in an orientation of the drawings which allows the normal reading of the reference signs. The drawings should not necessarily represent the forms of execution to scale. Rather, the drawings, where useful for explanation, are executed in schematic and/or slightly distorted form. The invention's features revealed in the description, in the drawings, and in the claims may be essential for any continuation of the invention, either individually or in any combination. The general idea of the invention is not limited to the exact form or detail of the preferred embodiments shown and described below or to a subject-matter which would be limited in comparison to the subject-matter of the claims. For the sake of simplicity, identical or similar parts or parts with identical or similar functions are hereinafter referred to by the same reference signs.

Further details and advantages shall now be described in connection with the drawings.

BRIEF DESCRIPTION OF THE FIGURES

It is shown in

FIG. 44 representative images of a tibial nerve stained for axons (RT97, top) or inflammatory cells (Iba1, bottom).

DETAILED DESCRIPTION

Figure 1:
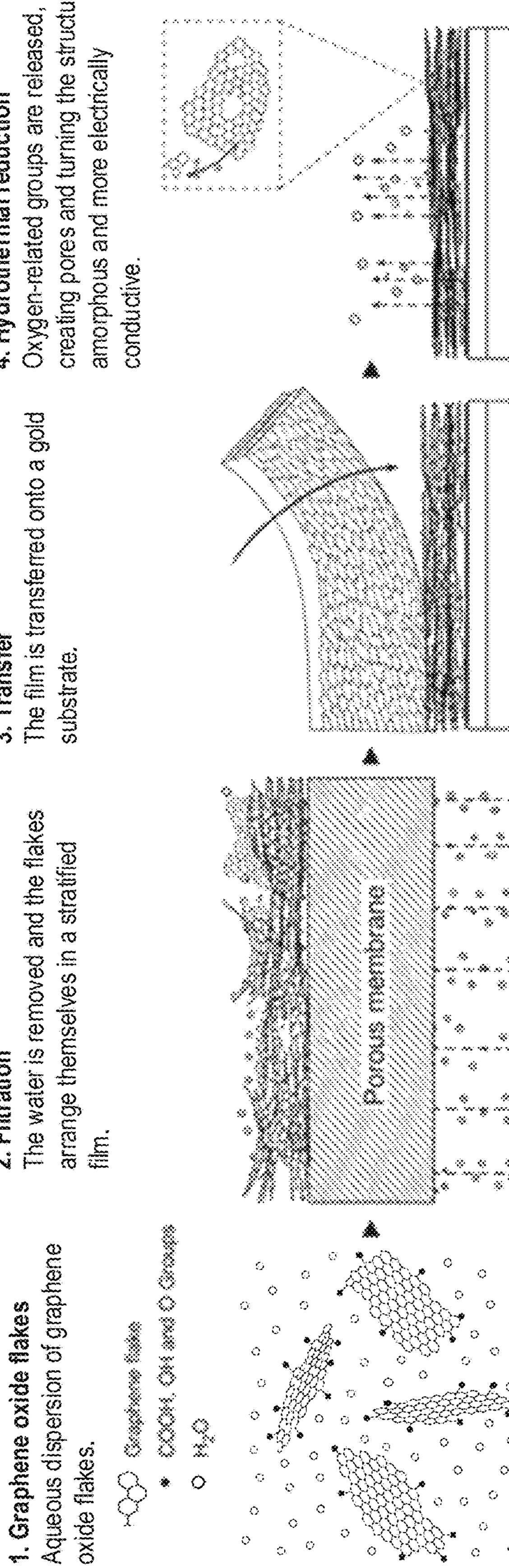
FIG. 1 a preparation process of a hydrothermally reduced graphene oxide structure (HTrGO) according to the present invention.

Neural implants offer therapeutic options to patients suffering from certain neurological disorders and other neural impairments (e.g. deafness, Parkinson's disease, amputations, etc.). Such technology currently consists of implantable devices that either electrically record or stimulate the nervous system using millimetre-scale metallic electrodes. To achieve broader acceptance of neural implants as a therapy, there is a need for a step-change improvement to their efficacy so that the therapeutic approach outweighs the risks from surgical implantation. Increasing neural interfacing resolution is at the core of such improvements.

The millimetre scale of the electrodes partially limits the quality of the recorded neural activity and the resolution of neural stimulation, which can limit the efficacy of the therapies.

To improve the interface with the nervous system, the electrode dimensions should be in the micrometre-scale. By reducing the electrode size to this scale, neural recordings could be captured at a higher spatial resolution, which could improve neural decoding. Additionally, the reduced electrode size would improve neural stimulation focality and expand the gamut of stimulation protocols available to re-create natural neural activation patterns occurring in healthy nervous tissue.

Currently, the electrode size is limited by the metals used as electrodes, such as platinum (Pt) or iridium (Ir). While these metallic interfaces can generally offer robust neural signal transduction when used in millimetre-scale electrodes, as the electrode size is reduced to the micrometre-scale, their performance dramatically drops due to their reduced electrochemical surface area, which increases the interfacial impedance and lowers the amount of charge that can be injected into the tissue. This translates into noisy recordings with low signal-to-noise ratio (SNR) because of the high contribution of the real part of the increased impedance. It also leads to the inability to stimulate the nervous tissue due to the combination of the low charge injection limit (CIL) of the metals and the reduced electrochemical surface area of the electrodes. Another challenge with metal electrodes is that they electrically interface with the nervous tissue with both faradaic and capacitive interactions. The presence of faradaic interactions is of great concern as they can change the pH of the media around them and dissolve the electrode into the tissue. Capacitive interactions, contributed by the charge and discharge of the double-layer capacitance at the electrode-electrolyte interface, are preferred because of their safer behaviour during stimulation and their reduced contribution to the noise during neural recordings.

To address the inherent neural interfacing resolution and potential safety concerns associated with large metallic electrodes, high-performance materials have been explored to miniaturize neural interfaces. Electrode surface modification strategies have been developed to increase the electrochemical surface area without increasing the geometric surface area of the electrode in order to improve the SNR and CIL of standard metal electrodes. To avoid faradaic reactions, materials whose interface in aqueous media is capacitive over a wide potential range, such as titanium nitride (TiN) or nanoporous boron-doped diamond, have been tested. However, TiN has been shown to exhibit low biocompatibility in certain cases and the nanoporous boron-doped diamond has challenging fabrication constraints. As an interesting alternative, conductive polymers (CP) such as poly(3,4-ethylenedioxythiophene) have been investigated in different combinations (PEDOT:PSS or PEDOT-CNT) due to their large electrochemical surface area, capacitive interface, and flexibility. However, the stability of these electrodes under continuous stimulation and in chronic settings remains debatable.

Due to its unique combination of superlative material properties, graphene has emerged as an attractive candidate material used for electrode fabrication in chronic bidirectional neural interface. Graphene, a monolayer of $sp^2$ hybridised carbon atoms, is one of the strongest, more electrically conductive and stable materials known to date. In the particular field of neural interfaces, graphene electrodes offer a capacitive interaction in aqueous media over a wide potential window and mechanical flexibility. Single-layer graphene microelectrodes have been used for neural interfacing applications, however the limited electrochemical performance of this carbon monolayer constrains the potential for miniaturization. As a result, porous materials based on graphene and reduced graphene oxide (rGO) have been developed in efforts to increase the electrochemical surface area and provide spatially focal neural recording and stimulation. Current achievements have lowered the impedance and increased the CIL of graphene-based electrodes. However, only bulky electrodes have been demonstrated, which limits the potential to integrate the technology into dense arrays for use with anatomically congruent neural interfaces.

Thus, in the following it first is described a hydrothermally reduced graphene oxide (HTrGO) structure according to the present invention, usable for a graphene-based thin-film electrode, that is designed to overcome the limitations of existing electrode structures or materials used for neural interfacing so far. The electrochemical capacitance of electrode comprising said structure has been increased by a factor $10^4$ compared to monolayer graphene.

Further, a wafer-scale fabrication process of flexible neural probes for high spatial resolution neural recording and stimulation is demonstrated as well. The new microelectrodes exhibit low impedance, high CIL, and long-term stimulation stability in saline. The performance of fabricated electrodes is further shown acutely in vivo for bidirectional neural interfacing in rodents.

Epicortical recording experiments performed with the electrodes comprising the structure according to the present invention exhibit low intrinsic noise and high SNR ratio at the limit of currently available electronic equipment.

Additionally, neural stimulation via intraneural electrode implants is demonstrated to activate specific subsets of axons within the fascicles of the sciatic nerve with low current thresholds and high selectivity.

Moreover, the results of two chronic in vivo biocompatibility studies performed with epicortical (up to 12 weeks) and intraneural (up to 8 weeks) electrode implantation are presented.

It can be stated already in advance that the new structure for electrodes according to the present invention and the corresponding electrodes are suitable for chronic implantation to the nervous system, inducing no significant damage, nor neuroinflammatory responses.

Material Synthesis and Device Fabrication

FIG. 1 shows the preparing steps of a hydrothermally reduced graphene oxide (HTrGO) structure.

Initially, a graphene oxide (GO) solution is provided comprising graphene flakes having COOH-, OH- and O-groups and the graphene flakes are dispersed in water ($H_2O$). In FIG. 1 at the left in the section "1. Graphene oxide flakes" thus a aqueous dispersion of graphene oxide flakes is shown and this forms the starting point of the method.

The concentration of GO in the solution is from 0.001 to 5 mg/mL.

In a first preparation step (in FIG. 1 the second section from the left, i.e. "2. Filtration"), the graphene oxide solution is filtered through a porous membrane thereby forming a GO structure on the membrane top. Here the water is removed and the flakes arrange themselves in a stratified film on the porous membrane.

The volume filtered may be from 5 to 1000 mL. In a second preparation step, the GO structure from the membrane is transferred onto a sacrificial substrate. As shown in the embodiment of FIG. 1 (third section from the left in FIG. 1, "3. Transfer"), the stratified film of graphene flakes is transferred onto a gold substrate.

So, the GO film is placed between the membrane at the top and the sacrificial substrate (i.e. the gold substrate) at the bottom.

After the transfer, the membrane is removed, whereby the GO structure remains attached onto the sacrificial substrate.

In a third preparation step (4. Section in FIG. 1, Hydrothermal reduction), the GO structure is hydrothermally reduced to form a HTrGO structure. Oxygen-related groups are released, creating pores and turning the structure amorphous and more electrically conductive. In particular, this happens at a temperature from 100 to 240° C., under a pressure from $10^5$ to $4 \cdot 10^8$ Pa, for a time period from 1 min to 24 h, and in the presence of water. Finally, the HTrGO structure is detached from the sacrificial substrate and is adapted to the electrode size to be used.

For the preparation of a possible embodiment of the HTrGO structure or material according to the present invention, an aqueous graphene oxide (GO) solution (Angstron Materials, N002-PS-1.0) is diluted in deionised water to obtain a 0.15 mg/mL solution. 20 mL of the diluted solution is vacuum filtered through a 47 mm diameter nitrocellulose membrane (Millipore, VSWP04700) with pores of 0.025 μm, forming a thick film of GO of about 2 μm. Once the film and the membrane dried out, the membrane is placed against the target substrate (e.g. a silicon wafer), with the GO film facing the substrate. The membrane is hydrated from the back side with DI water and gently pressed against the substrate. Next, the membrane is dried by blowing it with nitrogen and carefully peeled off, leaving the GO film attached on the substrate. Finally, the GO film-substrate stack is placed in sterilization pouches and hydrothermally reduced using an autoclave at 134° C. for 3 hours to form the HTrGO structure. To minimize the total thickness of an implant, a HTrGO structure of around 1 μm thickness is preferably used.

In a further step, an electrochemical activation is conducted.

The step of electrochemically activating comprises at least partially sweeping cyclically an electrical potential around a potential equilibrium within a plurality of predetermined ranges.

The ranges are predetermined such that Faradaic reactions being avoided.

The step of electrochemically activating comprises charged ions permeating into the stack, thereby preferably losing their solvation shell (see below especially in connection with FIG. 14).

The predetermined ranges are consecutive, wherein each succeeding range is equal to or greater than its preceding range.

Further, the number of sweeping cycles within each succeeding range is equal to or greater than the number of sweeping cycles within its preceding range.

Figure 2:
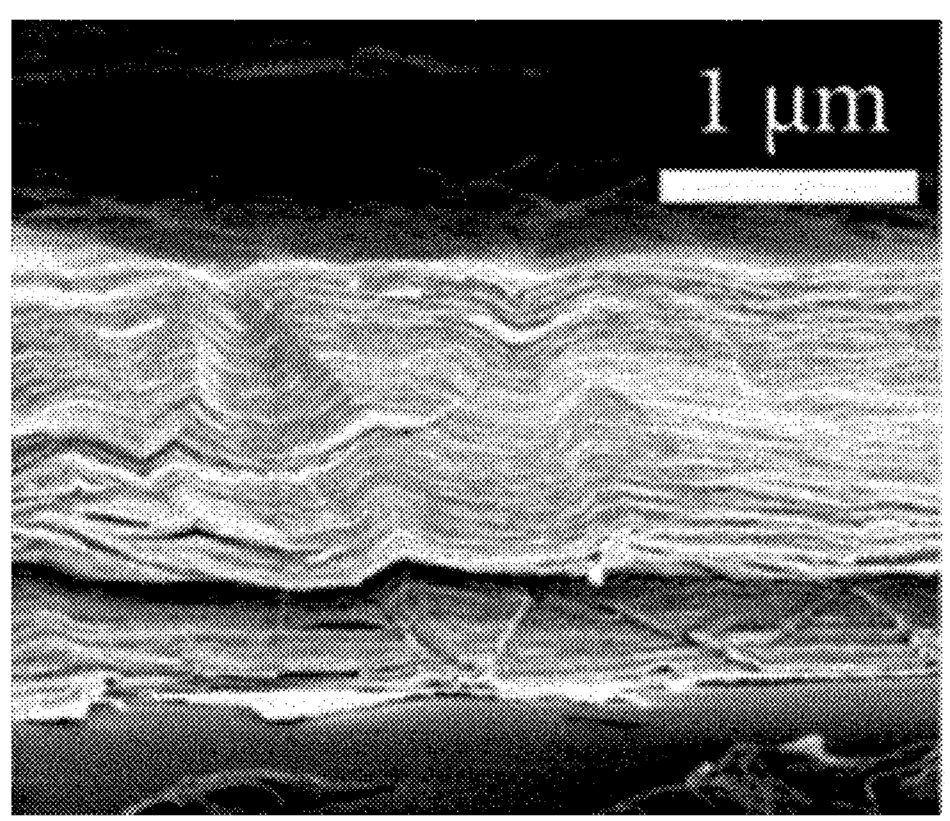
FIG. 2 a SEM micrograph of a cross section of the HTrGO structure according to the present invention.

FIG. 2 shows a cross section of the structure or material observed under the scanning electron microscope (SEM), revealing horizontally stacked flakes on top of each other.

Figure 3:
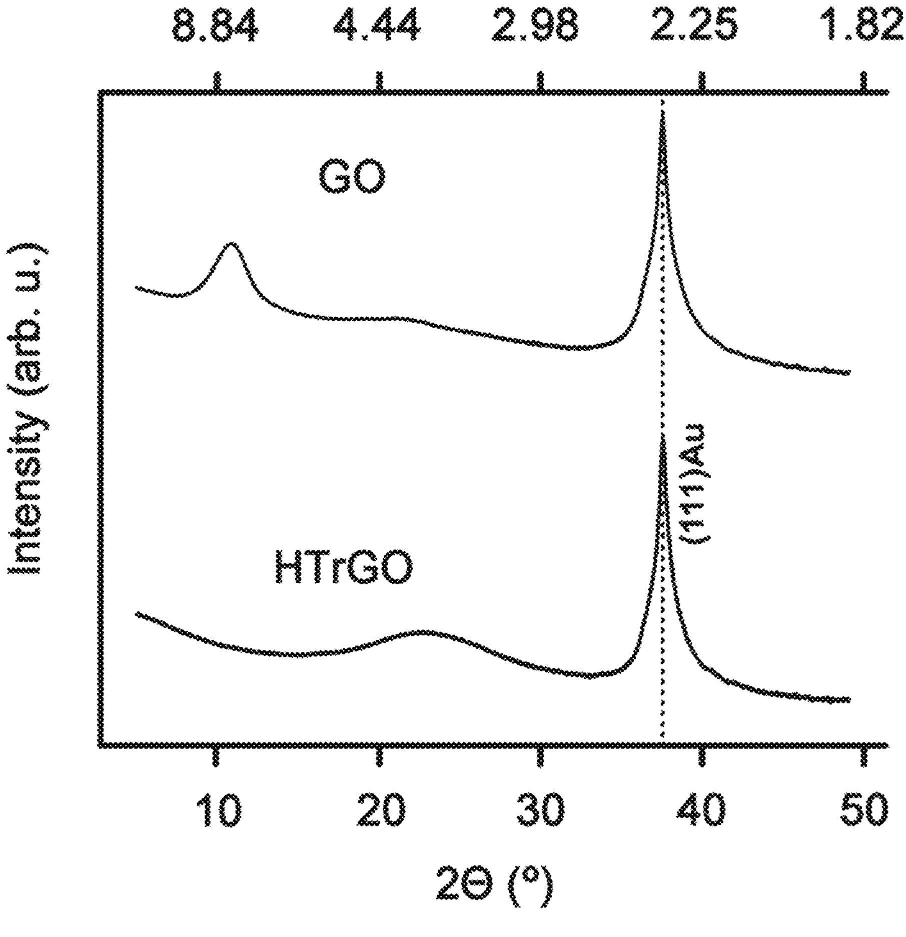
FIG. 3 results of a X-ray diffraction (XRD) measurement of a graphene oxide (GO) structure and HTrGO structure according to the present invention.

The stacking distance between flakes was investigated by X-ray diffraction (XRD), as shown in FIG. 3, before and after the hydrothermal reduction of the GO film to the HTrGO structure, showing a decrease from 8.1±0.8 Å to 3.9±0.6 Å. This decrease is attributed to the removal of the oxygen groups from the basal plane of the flakes. XRD measurements (θ-2θ scan) were performed in a Materials Research Diffractometer (MRD) from Malvern PANalytical. This diffractometer has a horizontal omega-2theta goniometer (320 mm radius) in a four-circle geometry and it worked with a ceramic X-ray tube with Cu Kα anode (λ=1.540598 Å). The detector used is a Pixcel which is a fast X-ray detector based on Medipix2 technology.

Figure 4:
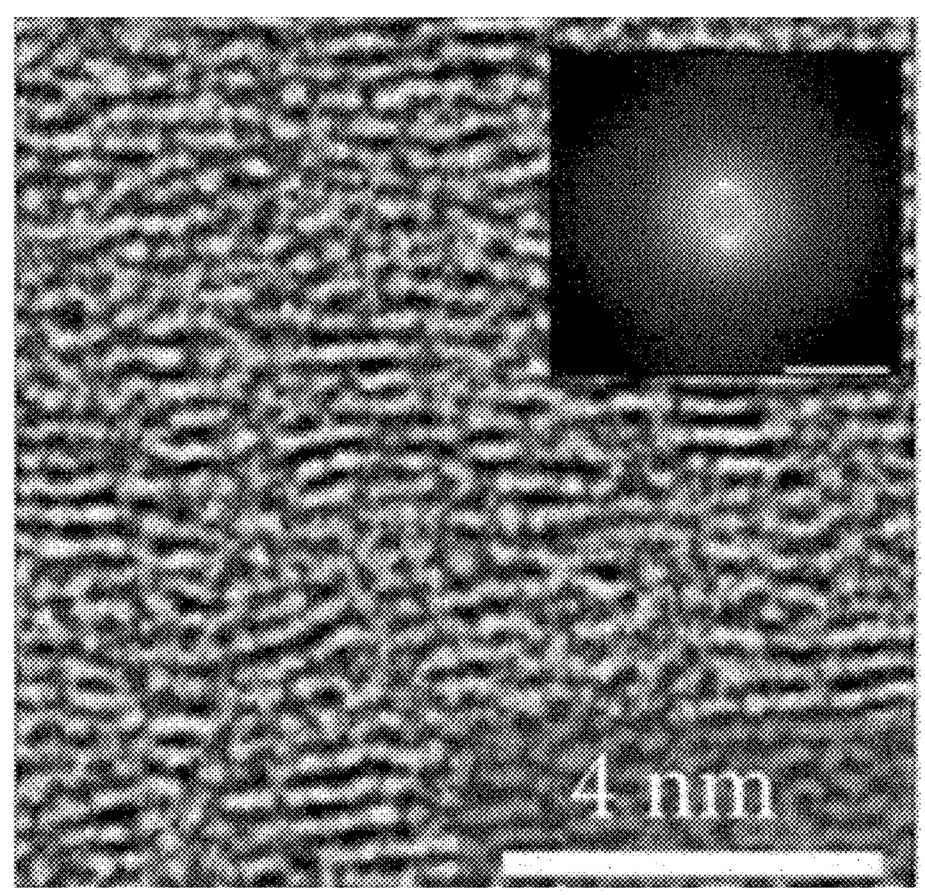
FIG. 4 a high resolution transmission electron microscopy (HRTEM) false-colour cross-sectional view of HTrGO structure according to the present invention and a corresponding power spectrum showing two symmetric diffuse spots that indicate preferred stacking direction in the material and slight fluctuation of the flakes interplanar distance.

The nanostructure cross-section of HTrGO structure is further investigated by high resolution transmission electron microscopy (HRTEM), as presented in FIG. 4, after preparing a focused-ion beam (FIB) lamella, which confirmed the stacked configuration of the flakes and the presence of nanometre-scale pores that connect the capillaries between flake planes. The power spectrum (Fast Fourier Transform) analysis of lower magnification HRTEM images indicates that the stacked configuration extends across the bulk of the material, with the distance between flakes close to 4 Å. The structural analyses were performed by means of Transmission Electron Microscopy using a TECNAI F20 TEM operated at 200 kV, including HRTEM and HAADF-STEM techniques.

Figure 5:
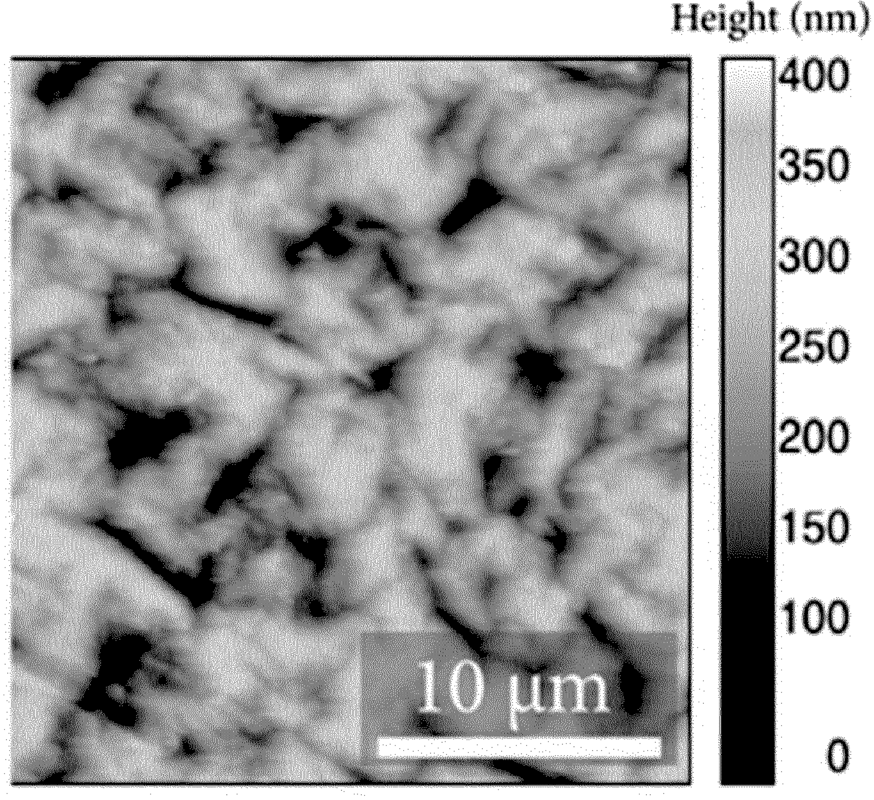
FIG. 5 an atomic force microscope (AFM) image revealing roughness of the upper surface of the HTrGO structure according to the present invention.

Beyond the internal structure of the HTrGO structure, understanding the topography and atomic composition of the outer surface is of particular importance because this will be in direct contact with biological tissue. Atomic force microscope (AFM) measurements, shown in FIG. 5, reveal a surface with a root square mean roughness as low as 55 nm. This value is expected to prevent tissue damage as well as promote adhesion and proliferation of cells while minimizing interaction with bacteria.

Figure 6:
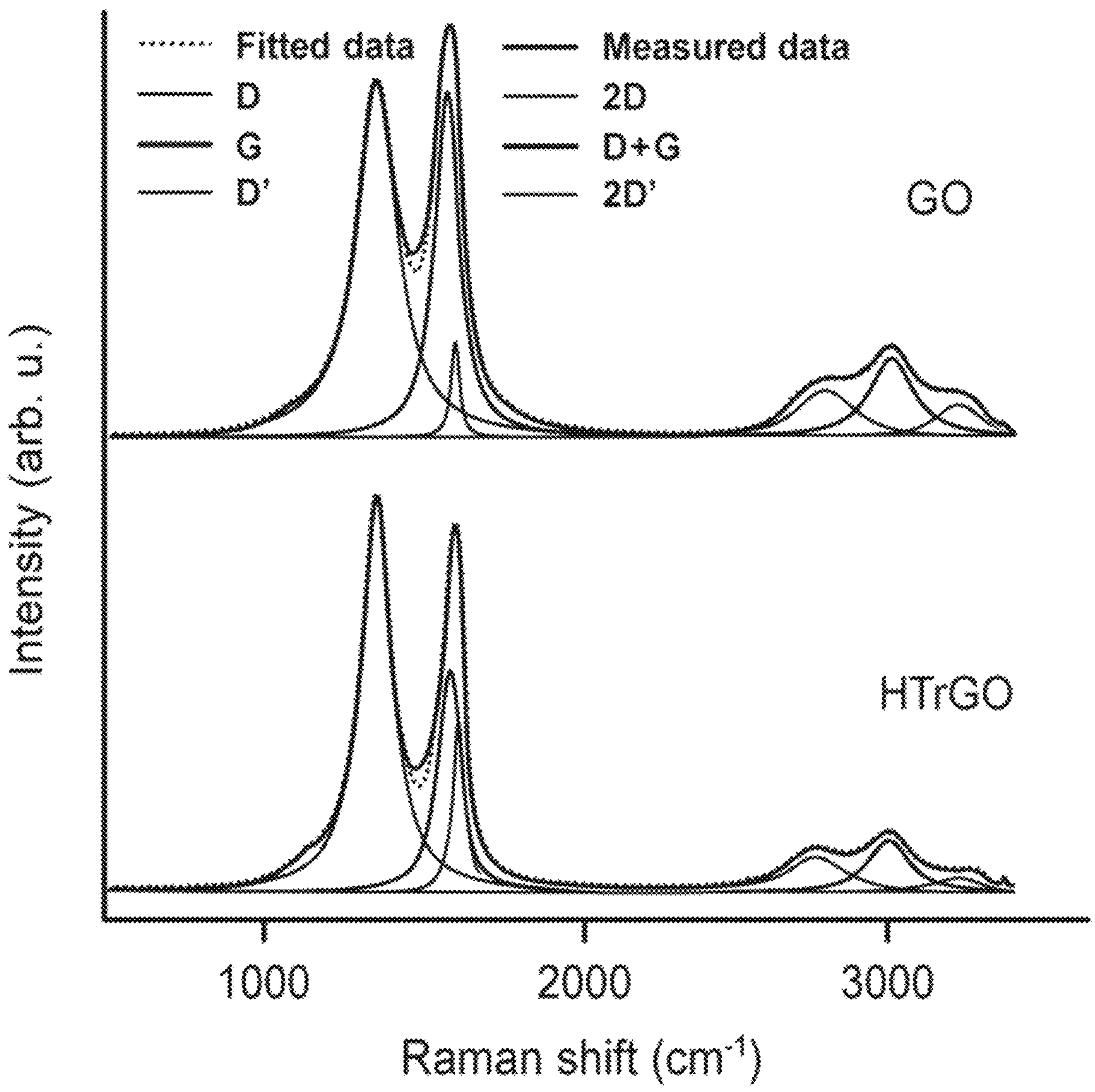
FIG. 6 Raman spectra of the GO and HTrGO structure according to the present invention.

Further assessment of the HTrGO structure was achieved using Raman spectroscopy. The Raman spectrograms in FIG. 6 show the G band associated with carbon (1582 $cm^{-1}$), and the D band related to defects in the graphene basal plane (1350 $cm^{-1}$). The slightly higher defects content observed in the HTrGO structure compared to untreated GO and their nature, associated to vacancies, is tentatively explained by the effect of the hydrothermal reduction of the functionalizing oxygen containing groups, which is assumed to pull out part of the basal plane, creating holes in the reduced GO flakes. The holes interconnect the capillaries between the flakes planes and are at the origin of the highly enlarged electrochemical surface area (EASA) of the material.

Figure 7:
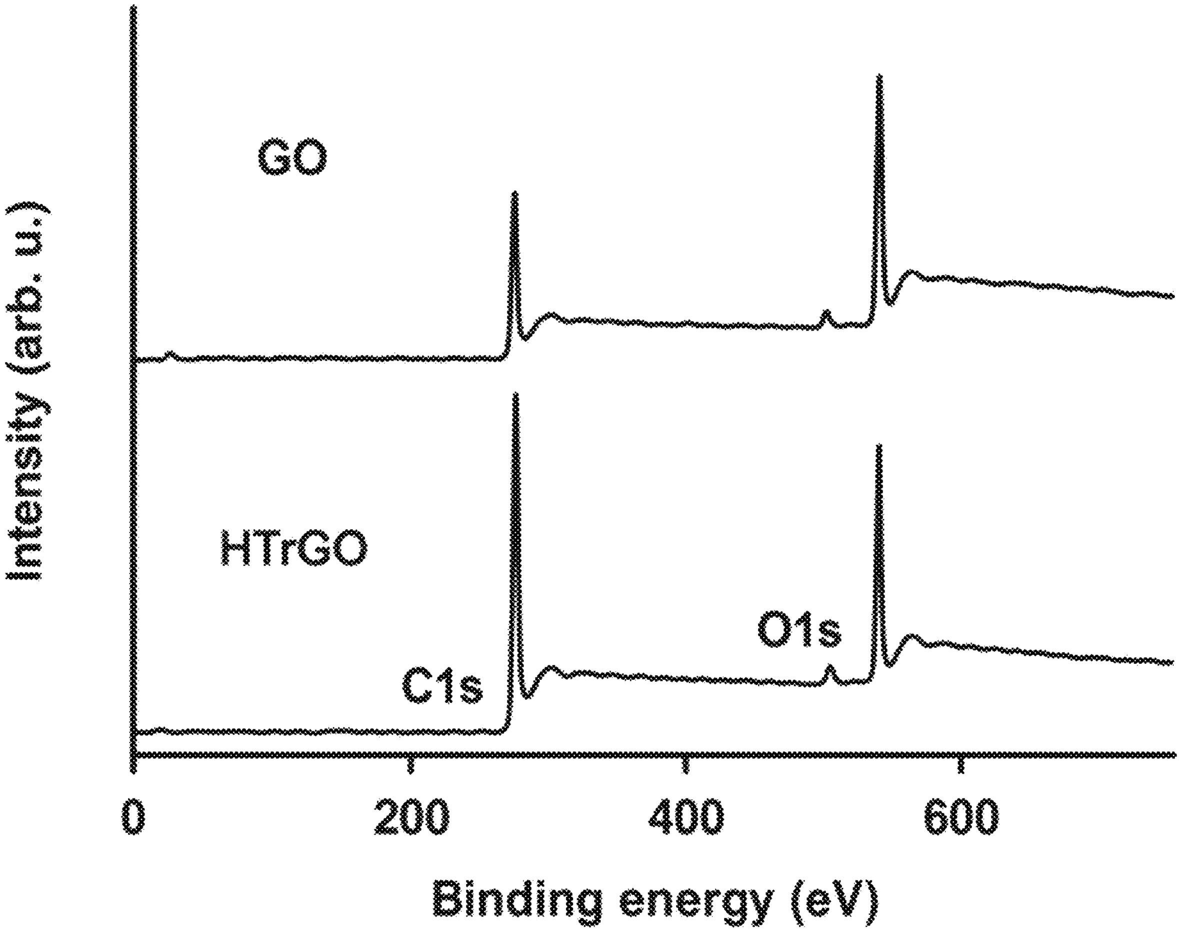
FIG. 7 an X-ray photoelectron spectroscopy (XPS) full spectrum of the HTrGO structure according to the present invention.

The outer and inner chemical composition of the HTrGO structure was studied by X-ray photoelectron spectroscopy (XPS) and electron energy loss spectroscopy (EELS), respectively. The STEM-EELS experiment was performed in a Tecnai F20 microscope working at 200 KeV, with 5 mm aperture, 30 mm camera length, convergence angle 12.7 mrad and collection angle 87.6 mrad. 0.5 eV/px and 250 eV as starting energy were used in the core-loss acquisition; Si k-edge expected at 1839 eV, the Pt M-edge at 2122 CV and the Au M-edge at 2206 eV was not acquired. The relative C—O atomic composition has been obtained focusing on the GO layer and assuming that the edges analyzed (C and O in our case) sum to 100%. The energy differential cross section has been computed using the Hartree-Slater model and the background using a power low model. FIG. 7 shows XPS survey spectra which confirms the reduction process during the hydrothermal treatment, decreasing the oxygen content from 25% in the GO structure to 12% after the hydrothermal process.

Figure 8:
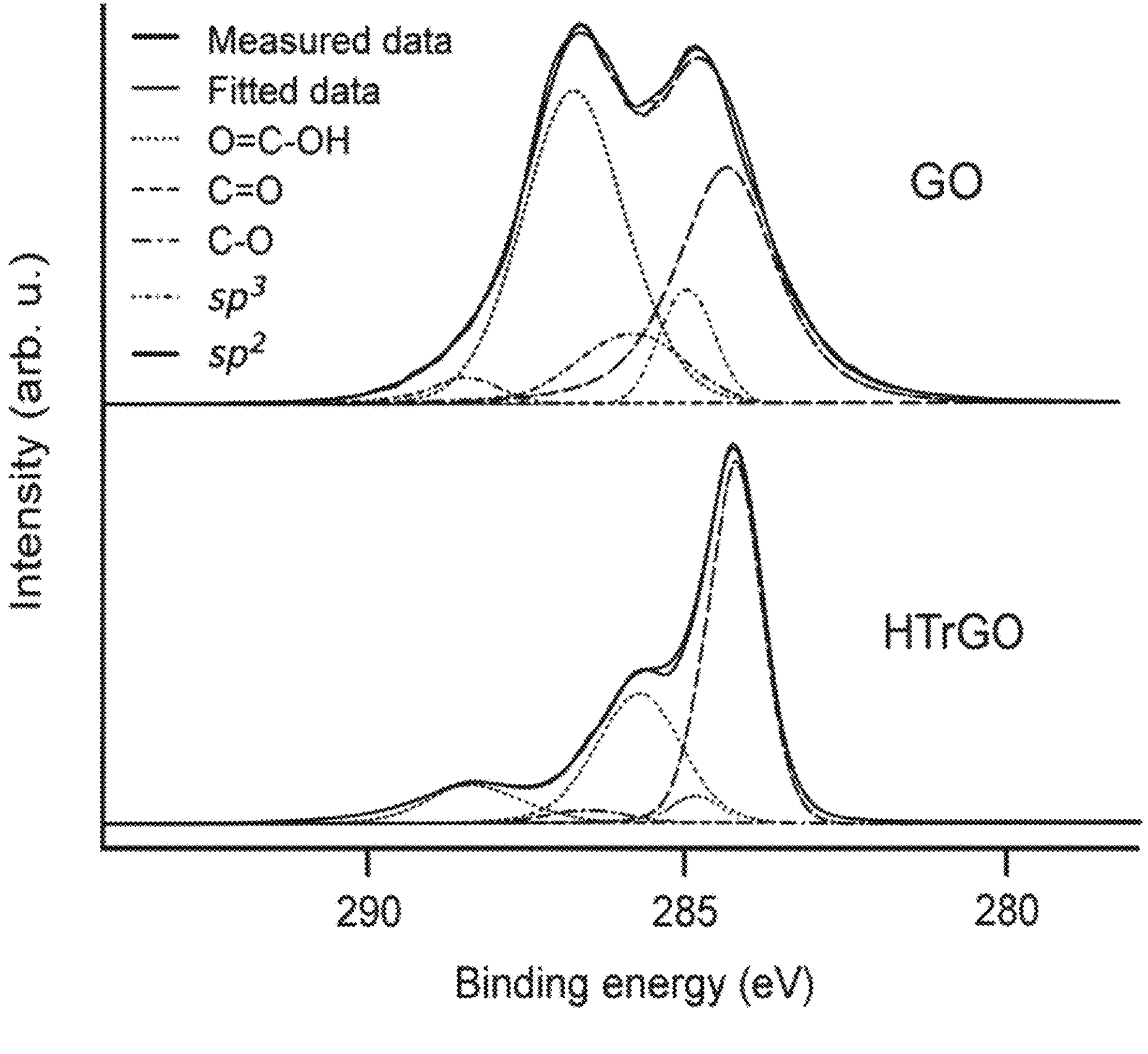
FIG. 8 the C1s peak of (top) GO structure and (bottom) HTrGO structure of FIG. 7.
Figure 9:
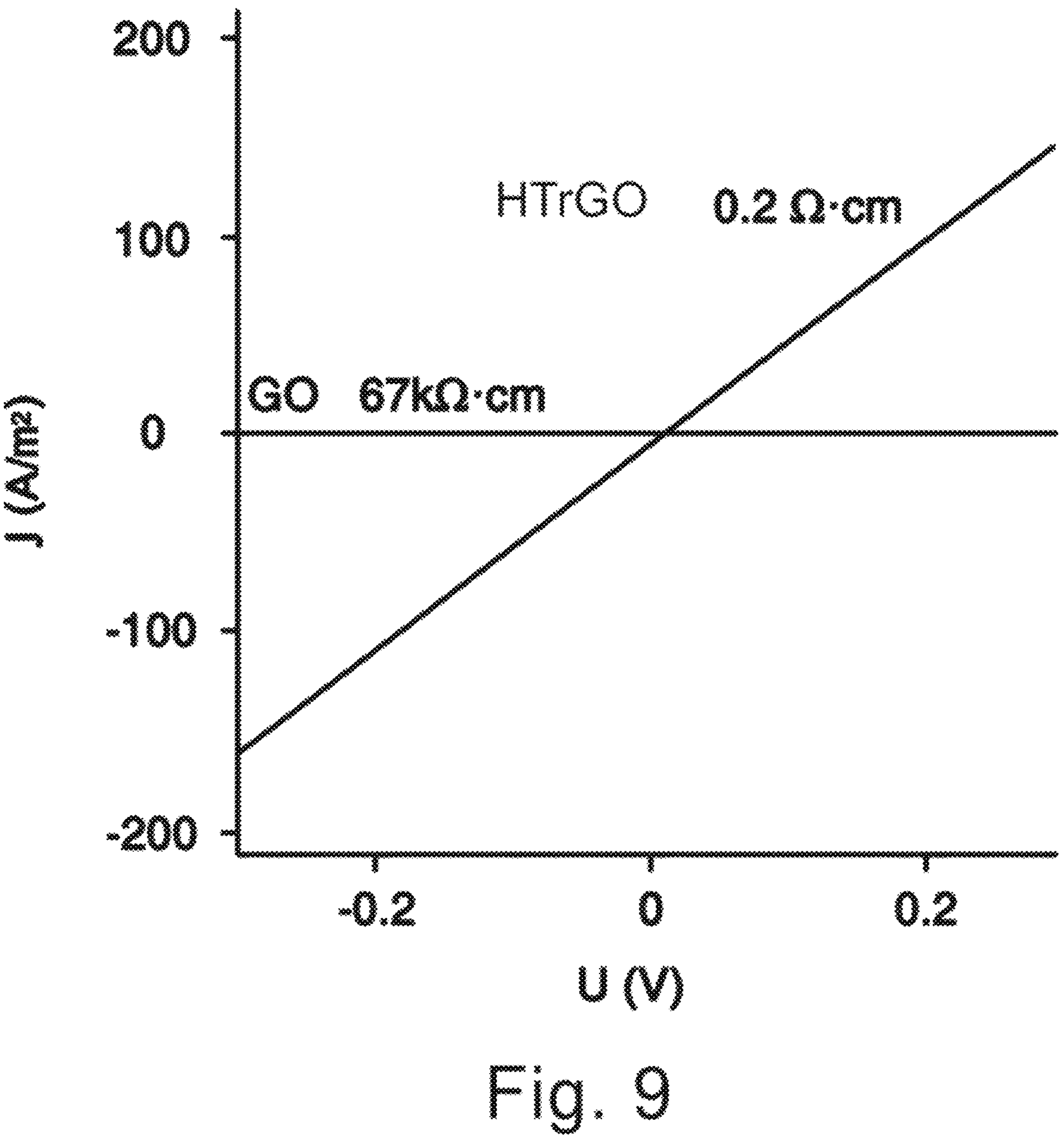
FIG. 9 conductivity measurement results of a GO structure and HTrGO structure according to the present invention.

High-resolution XPS measurements in the energy range of C1s peak are shown in FIG. 8. The C1s peak is deconvoluted according to the peaks associated to the $sp^2$ (284.5 eV) and $sp^3$ (285.0 eV) orbitals as well to the ones related to C—OH (285.8 eV), C═O (286.7 eV) and C(O)OH (288.5 eV) bondings. The analysis shows a strong decrease after the hydrothermal treatment of the C—O peak associated to epoxide groups; but a small contribution of C—OH, C═O and C(O)OH due to hydroxyls, carbonyls and carboxyls remains after reduction. The deconvolution of the O1s peak confirms such behavior. The main contribution of the C1s signal after the hydrothermal reduction, however, comes from $sp^2$ hybridized C—C orbitals. The composition deep inside the material was further investigated using EELS in Scanning TEM (STEM) mode, in the FIB cross-section lamella. The cross-sectional study reveals carbon and oxygen relative atomic contents of 85% and 15%, respectively, in the bulk of the structure, which concurs with the XPS data. The low oxygen content and robustness of $sp^2$ bondings are particularly beneficial for the biocompatibility of the material. Additionally, hydrothermal reduction of GO to the HTrGO structure leads to a decrease in the measured resistivity from 66 kΩ cm to 0.2 Ω·cm, as can be seen in FIG. 9.

For in vivo studies, the following preparation process was developed to integrate arrays of HTrGO structure microelectrodes (cf. FIG. 10*a*) into flexible devices (total thickness of 13 μm) using the biocompatible and flexible polymer, polyimide (PI)37, as substrate and insulation, and Au for the tracks:

The devices were fabricated on 4" Si/SiO2 (400 μm/1 μm) wafers. First, a 10 μm thick layer of polyimide (PI-2611, HD MicroSystems) was spin coated on the wafer and baked in an atmosphere rich in nitrogen at 350° C. for 30 minutes. Metallic traces were patterned using optical lithography of the image reversal photoresist (AZ5214, Microchemicals GmbH, Germany). Electron-beam evaporation was used to deposit 20 nm of Ti and 200 of Au. After transferring of the GO film, the film was then structured using a 100 nm thick aluminium mask. Columns of aluminum were e-beam evaporated and defined on top of the future microelectrodes via lift off by using a negative photoresist (nLOF 2070, Microchemicals GmbH, Germany). Next, the GO film was etched everywhere apart from the future microelectrodes using an oxygen reactive ion etching (RIE) for 5 minutes at 500 W. The protecting Al columns were subsequently etched with a diluted solution of phosphoric and nitric acids. After, a 3 μm thick layer of PI-2611 was deposited onto the wafer and baked as done before. PI-2611 openings on the microelectrode were then defined using a positive thick photoresist (AZ9260, Microchemicals GmbH, Germany) that acted as a mask for a subsequent oxygen RIE. Later, the devices were patterned on the PI layer using again AZ9260 photoresist and RIE. The photoresist layer was then removed in acetone and the wafer cleaned in isopropyl alcohol and dried out. Finally, the devices were peeled off from the wafer, placed in sterilization pouches and hydrothermally reduced at 134° C. in a standard autoclave for 3 hours to form the HTrGO structure.

Figure 10:
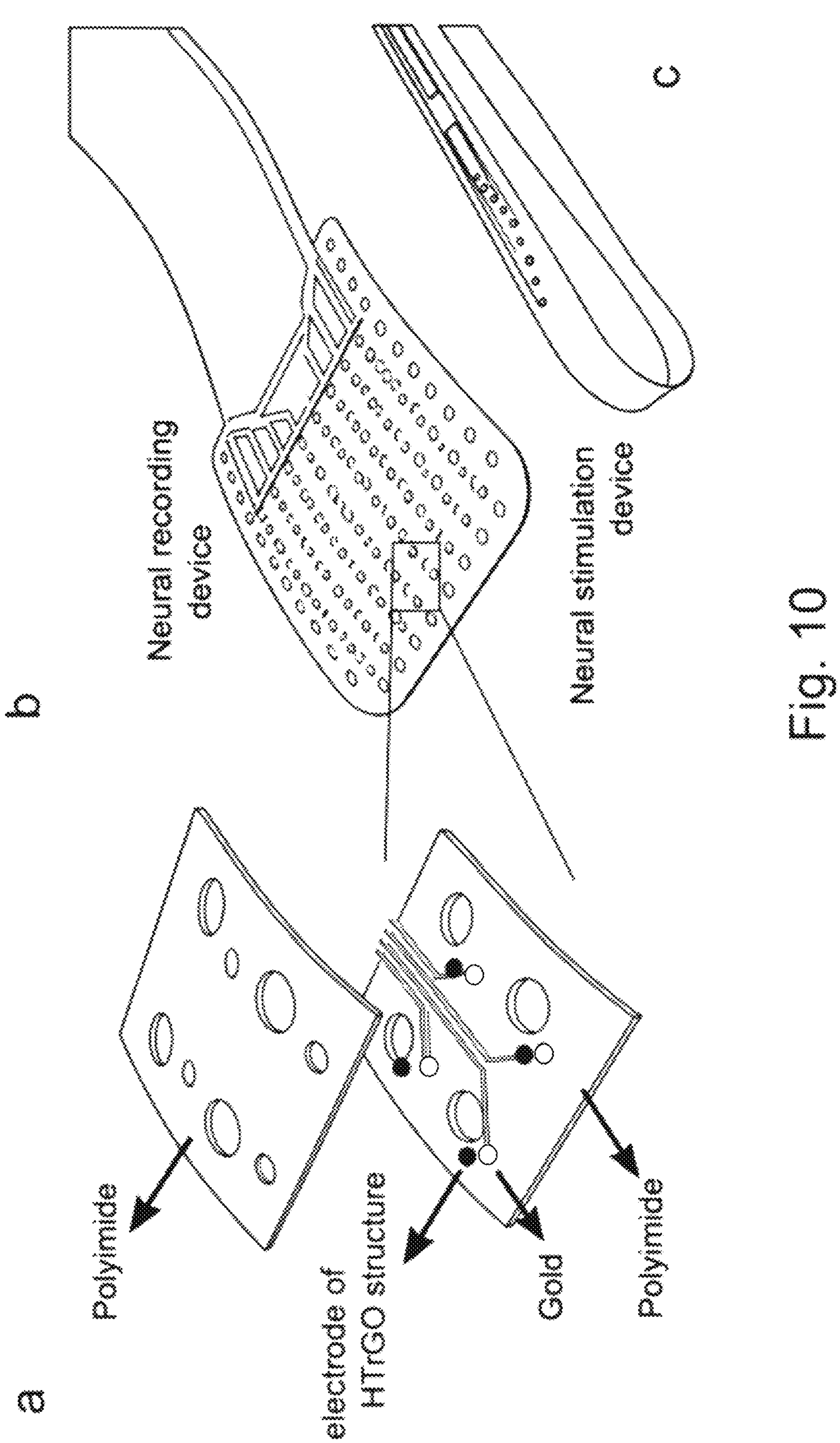
FIG. 10 design and types of flexible electrodes arrays comprising the HTrGO structure according to the present invention.
Figure 11:
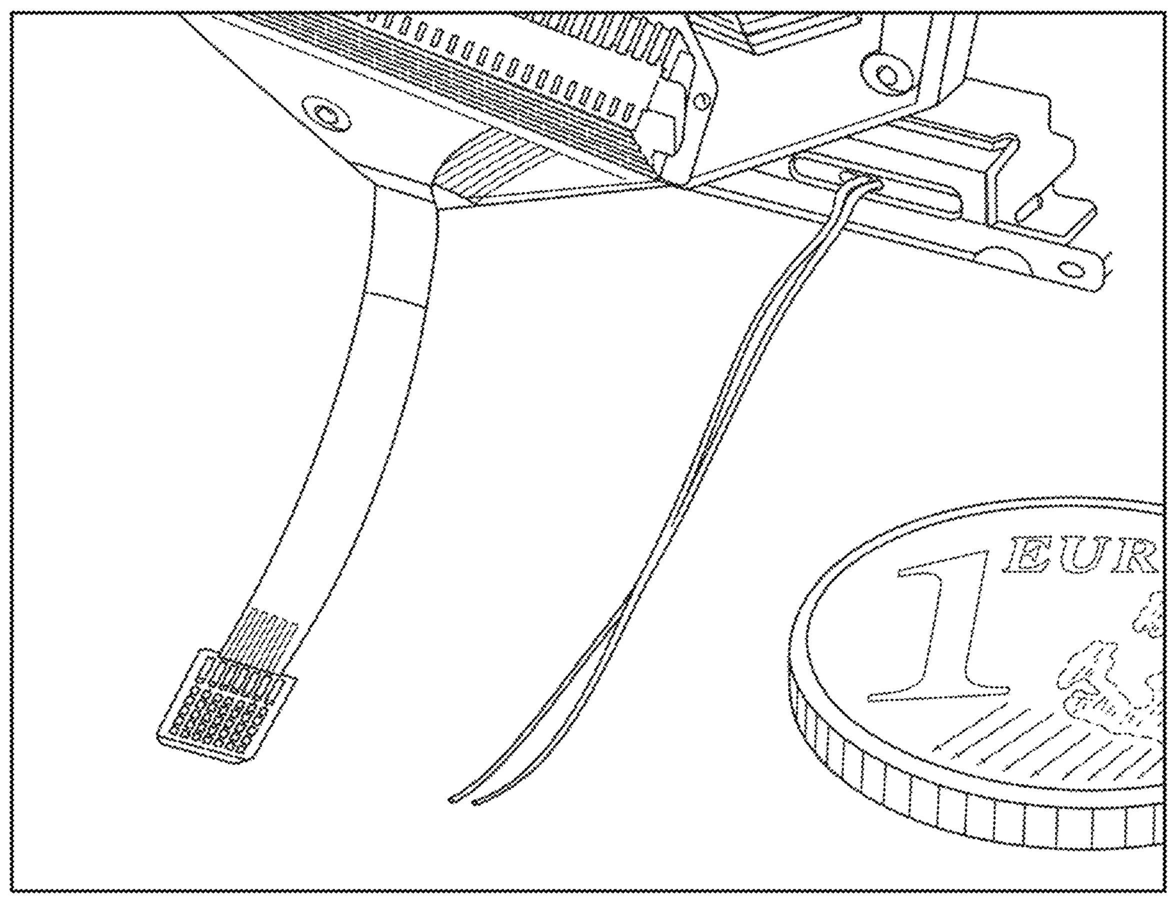
FIG. 11 the two flexible electrodes arrays types of FIGS. 10*b* and 10*c;*
Figure 12:
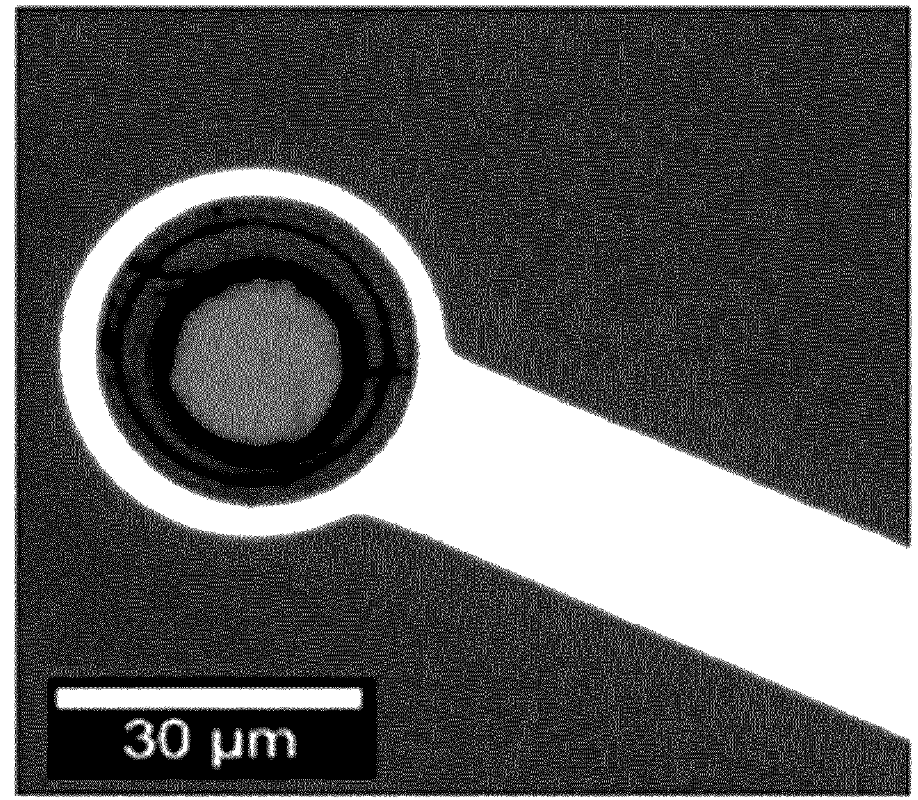
FIG. 12 a photography of a flexible implant comprising the HTrGO structure according to the present invention.

Two different designs with 25 μm diameter microelectrodes were fabricated. FIG. 10*b* shows a micro-electrocorticography (μECoG) array with 64 electrodes organized in an 8×8 grid with a pitch of 300 μm to record epicortical neural activity from rodents. FIG. 10*c* shows a transverse intrafascicular multichannel electrode (TIME) device with two linear arrays of 9 microelectrodes separated 135 μm from each other designed to selectively stimulate different muscular fascicles inside the sciatic nerve in rodents. The devices were highly flexible (cf. FIG. 11) and microelectrodes as small as 25 μm in diameter were successfully integrated with yield above 90% as shown in FIG. 12.

Generally speaking, an electrode device for detecting, receiving and/or inducing electrical signals can be obtained this way, preferably from and/or into brain tissue, and more preferably from and/or into single neural cells, wherein the electrode comprises the hydrothermally reduced graphene oxide structure as described in this disclosure.

For example, the hydrothermally reduced graphene oxide structure can have a diameter of 25 μm or less and provides a charge injection limit from 2 mC/cm$^2$ to 10 mC/cm$^2$ and/or an impedance of 10 to 100 kΩ at a frequency of 1 kHz in an electrolyte system.

The electrode device can be used in mammals and especially also for the treatment of human patients.

Electrochemical Characterization

Figure 13:
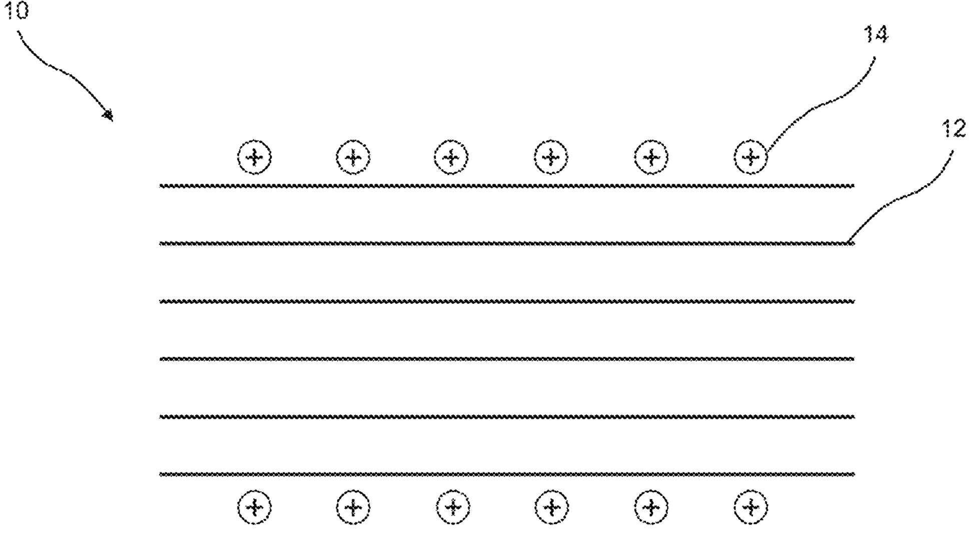
FIG. 13 an embodiment of an electrochemically activated structure graphene oxide structure.

In FIG. 13, a GO structure 10 is schematically shown forming a stack of GO layers 12. The charged ions 14 of an electrolyte system substantially arrange on the outer surfaces of the GO structure 10, since the distance between the GO layers 12 is partially not sufficient to allow charged ions 14 to pass between them.

In contrast thereto, a HTrGO structure 20 is schematically presented in FIG. 14, wherein the hydrothermal reduction corresponds to the steps as described in connection with FIG. 1. Due to the hydrothermal reduction, holes 26 could be formed into the planes of the GO layers 22 allowing charged ions 24 to immerse into the HTrGO structure, thereby increasing the EASA.

The holes 26 can have a diameter equal to or less than 10 nm.

Especially, the holes 26 are permeable for charged ions.

So, a hydrothermally reduced graphene oxide structure for neurostimulation, in particular for Cortical and/or Deep Brain Stimulation, comprising a stack of layered, hydrothermally reduced graphene oxide flakes, wherein the hydrothermally reduced graphene oxide structure (cf. e.g. FIG. 1) is electrochemically activated, is obtained.

Figure 14:
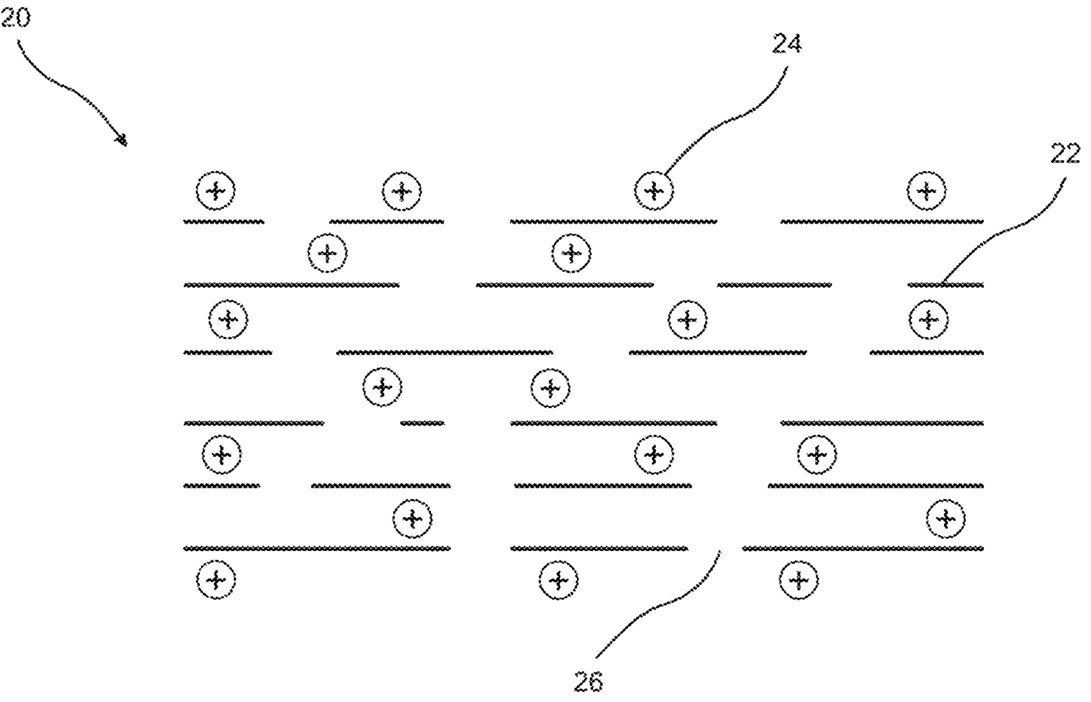
FIG. 14 an embodiment of an electrochemically activated structure and hydrothermally reduced graphene oxide structure according to the present invention.

As can be seen in FIG. 14, the charged ions are arranged between the layers of the reduced graphene oxide flakes and on the outer surfaces of the stack.

The distance between two consecutive layers is e.g. and as shown in the embodiment of FIG. 14 between 0.2 nm and 0.7 nm, preferably between 0.3 nm and 0.5 nm.

The thickness of the reduced graphene oxide structure is between 20 nm to 5 μm, preferably between 500 nm to 2000 nm.

Figure 15:
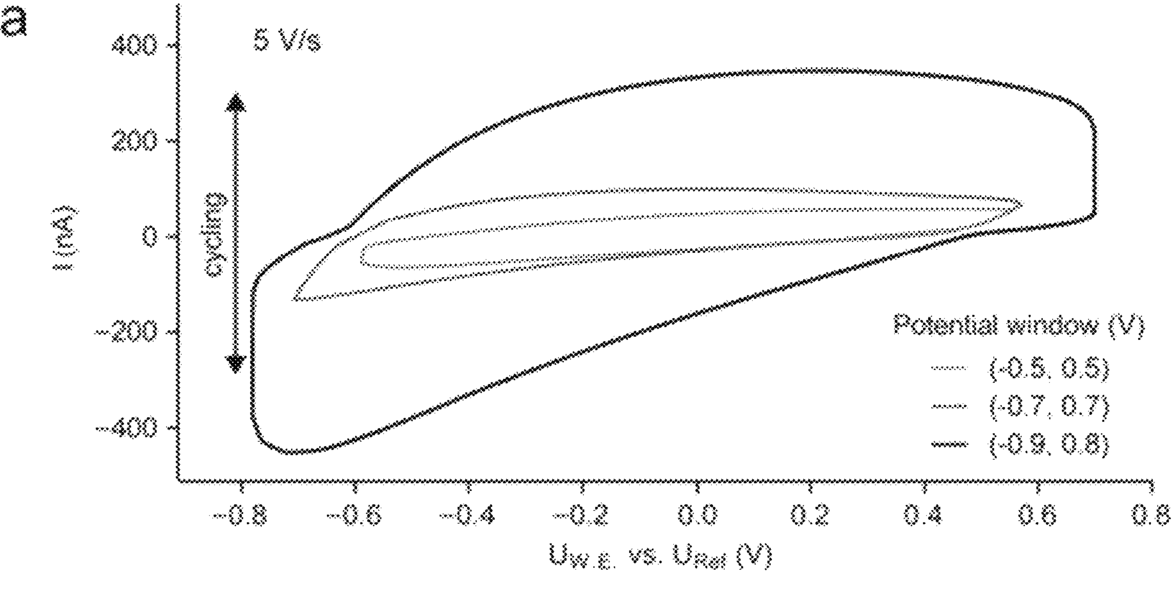
FIG. 15 a set of cyclic voltammetry to electrochemically activate the hydrothermally reduced graphene oxide structure applied to an electrode comprising the electrochemically active and hydrothermally reduced graphene oxide structure according to the present invention.
Figure 15:
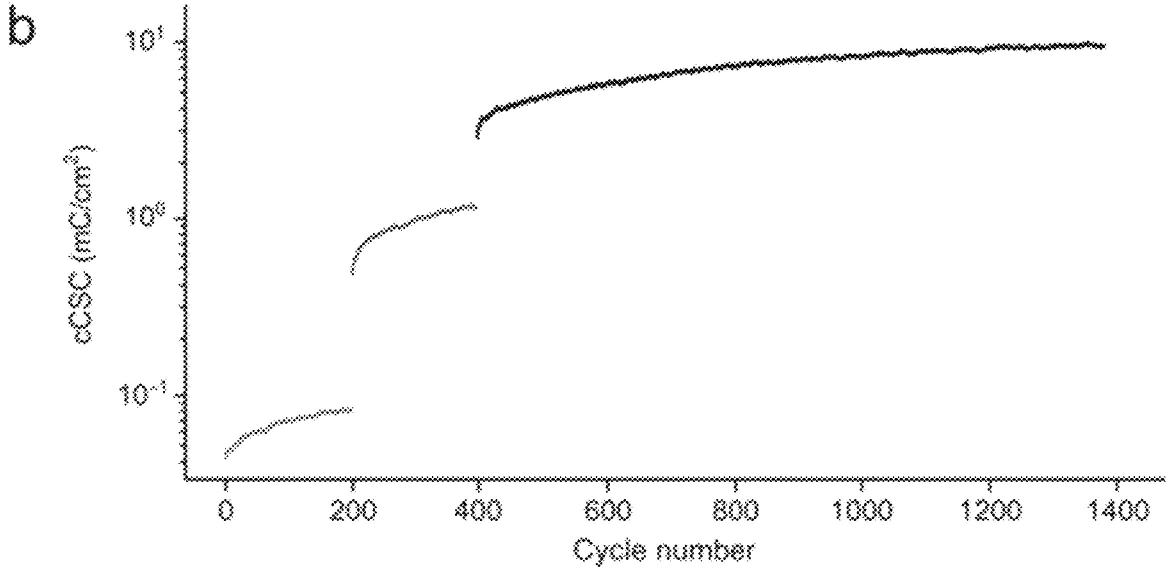

In FIG. 15, the increase of performance due to a set of cyclic voltammetry applied to an electrode having a diameter of 25 μm and comprising the HTrGO structure as defined above is presented, wherein the voltammetry was performed in a saline solution. To achieve the optimal performance, the electrode has to go through an electrochemical activation process as described before. FIG. 15*a* shows overlapped, the cyclic voltammetry of several hundreds cycles measured at 5 V/s over 3 successively expanding potential ranges. Starting with a conservative range of 1 V, between −0.5 V and 0.5 V. Within that range, no irreversible reactions were observed and the current behaved mostly flat, as expected for a capacitive interface. On the first cycle, a cCSC of 0.045 mC/cm$^2$ was obtained, as shown in FIG. 15*b*. From this value, an interfacial capacitance of 45 μF/cm$^2$ was calculated. Upon the subsequent 200 cycles, the current successively increased. Translated to capacitance, the value raised up to 65 μF/cm$^2$. Then, by expanding the potential range to ±0.7 V, the current and the cCSC increased about one order of magnitude, to 0.4 mC/cm$^2$ in the first cycle. During the following 200 cycles, the interfacial capacitance increased from 0.29 mF/cm$^2$ to 0.96 mF/cm$^2$. This increase however, is not linear. The rise mostly happened in the first 20 cycles and then it slowed down. Another expansion of the potential window to ranges between −0.9 V and 0.8 V led to a further larger increase of the current, the cCSC and the capacitance. Starting with a cCSc of about 3 mC/cm$^2$ and a capacitance of 1.8 mF/cm$^2$, after 1000 cycles these values increased to 11 mC/cm$^2$ and 6.5 mF/cm$^2$. Overall, the electrode performance increases three orders of magnitude upon the presented set of potential cycling.

Being the capacitive response a charge transfer mechanism that directly scales with the EASA, it is reasonable to assume that the increase in the performance upon cycling results from the increase of the electrolyte to it. Initially, it could be assumed that only the topmost layers can contribute to the current. The value of 45 μF/cm$^2$ is reasonable to come from a non-porous rGO surface, since this material is rougher and with more edges than single layer graphene. From that, it can be deduced that the HTrGO structure is not filled with the electrolyte by just immersing in it.

The observed increase of the electrochemical performance during cycling is due to a combination of the structural modifications caused by the hydrothermal reduction on the graphene flakes of the material and electrochemical and electrophoresis processes, which lead together to ionic sieve effects. Thus, the electrolyte ions access the graphene planes in the structure across the nanometre-scale holes created on the flakes during the hydrothermal reduction when the potential is shifted to certain values.

The electrochemical performance and stability of the 25 μm diameter HTrGO structure microelectrodes were further assessed in vitro in a phosphate buffer saline (PBS) solution, and compared to commercially-available microelectrodes (CAEs: poly-3,4-ethylenedioxythiophene (PEDOT)-carbon nanotube (CNT), ø 30 μm, Multi Channel Systems; titanium nitride (TiN), ø 30 μm, Multi Channel Systems; Platinum (Pt), ø 60 μm, NeuroNexus).

Figure 16:
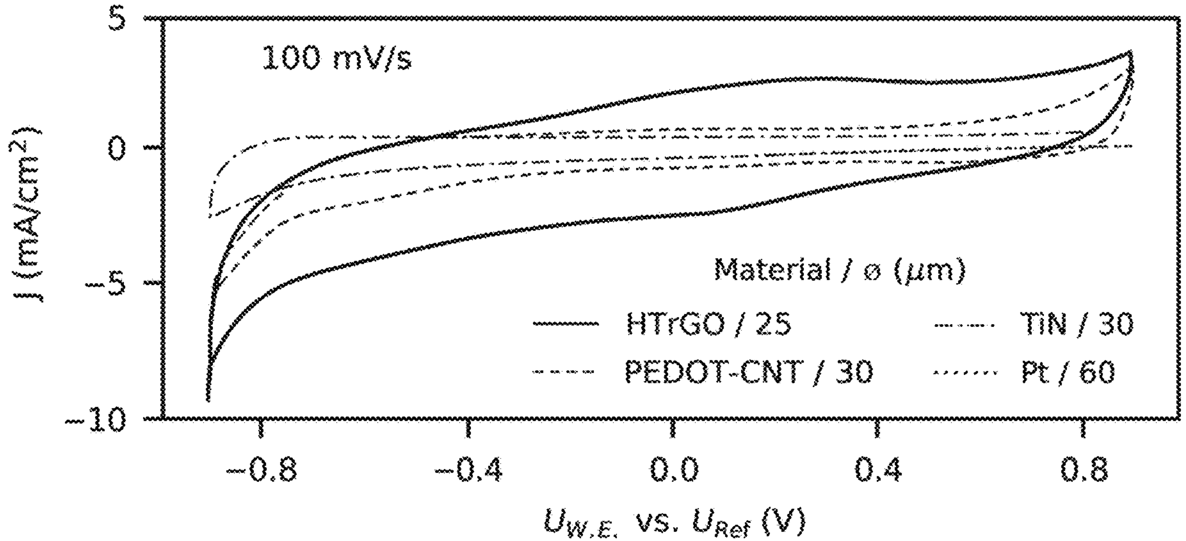
FIG. 16 a set of cyclic voltammetry at 100 mV/s of HTrGO structure microelectrodes and different commercially available electrodes (CAEs)
Figure 17:
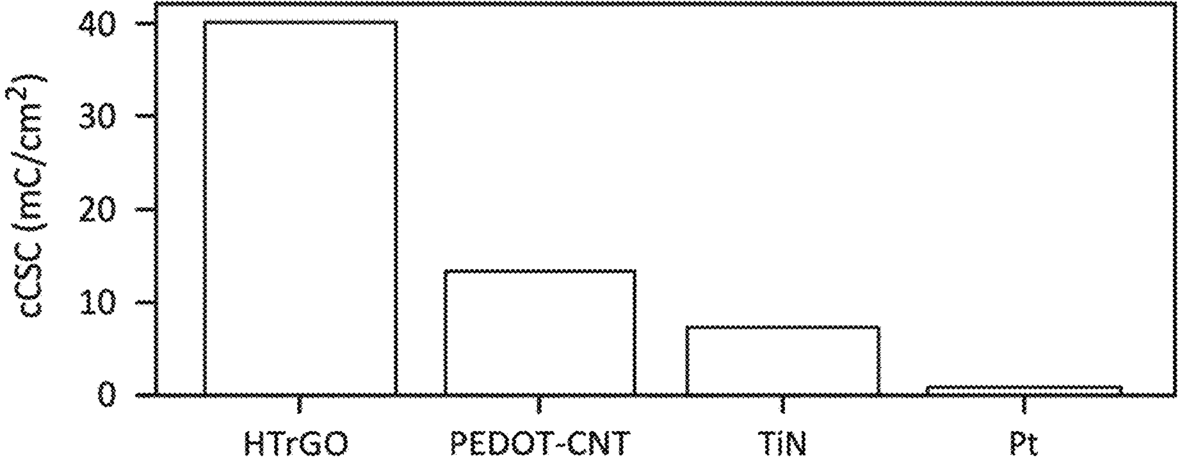
FIG. 17 a comparison of the cCSC due to cyclic voltammetry between different CAEs and the HTrGO structure electrode according to the present invention.

FIG. 16 shows the cyclic voltammetry (CV) between −0.9 and +0.9 V for HTrGO structure microelectrodes. Within this potential window the interface behaved capacitively and no significant faradaic reactions were identified. Similar interface behaviour was observed for PEDOT-CNT and TiN in the same potential window and for Pt between 0.2 and 0.8 V. The cathodic charge storage capacitance (cCSC) of HTrGO structure reached 40 mC/cm$^2$, which outperformed all three CAEs by a factor between 4 and 40, as can be inferred from FIG. 17.

Figure 18:
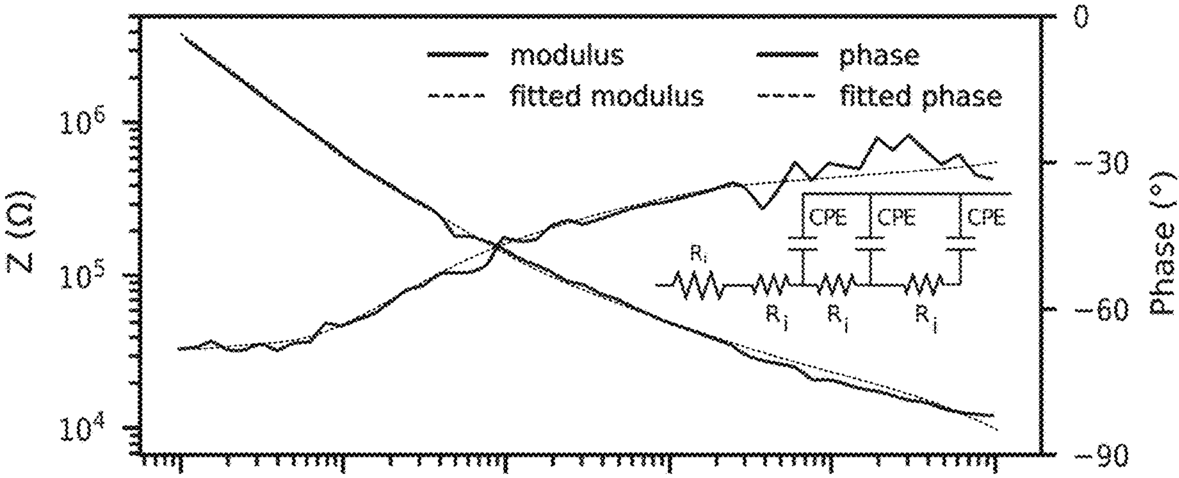
FIG. 18 a graph of the electrochemical impedance spectroscopy of an HTrGO structure microelectrode and fitting of the data using a distributed equivalent circuit of the system.
Figure 19:
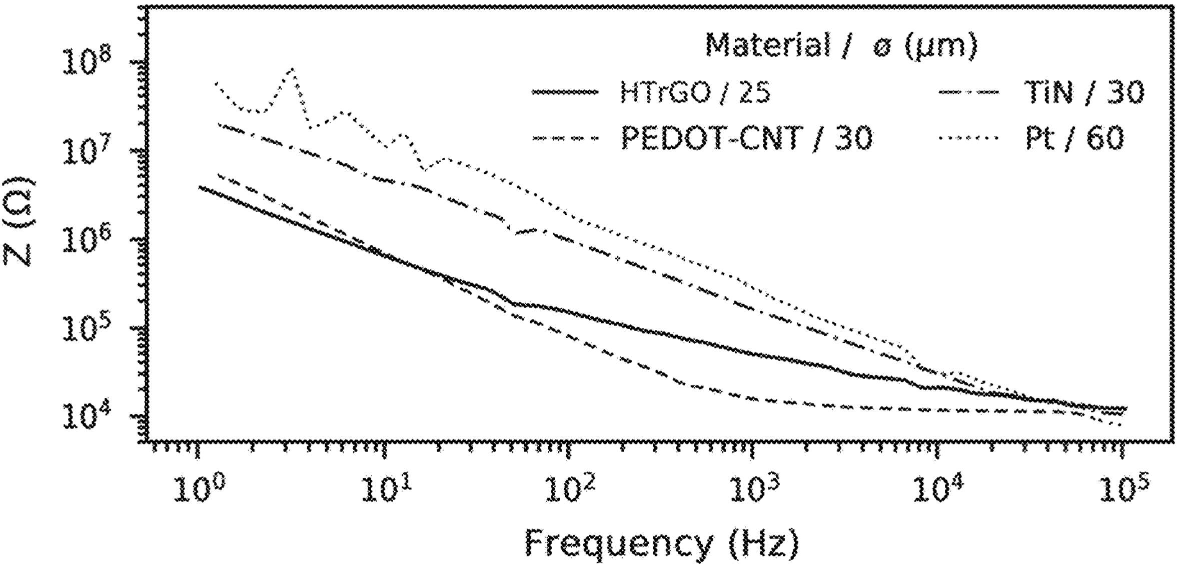
FIG. 19 an impedance spectroscopy comparison of the HTrGO structure electrode with CAEs.

FIG. 18 shows an impedance spectroscopy of the HTrGO structure. The data was fitted with an equivalent electric circuit in which the interface was modelled as a distributed constant phase element (CPE) and also taking into account the electrode resistivity (Ri) (cf. FIG. 18, inset). From the fitting, the interfacial capacitance was adjusted to 52 mF/cm$^2$, which corresponds to a $10^4$-fold increase with respect to the typical value of single-layer graphene (2 μF/cm$^2$). At 1 KHz, the HTrGO structure microelectrodes exhibited an impedance of 40 kΩ, which is in the range of the 20 kΩ impedance measured for PEDOT-CNT and significantly lower than the 160 kΩ and 245 kΩ impedances measured for TiN and Pt, respectively (cf. FIG. 19).

Figure 20:
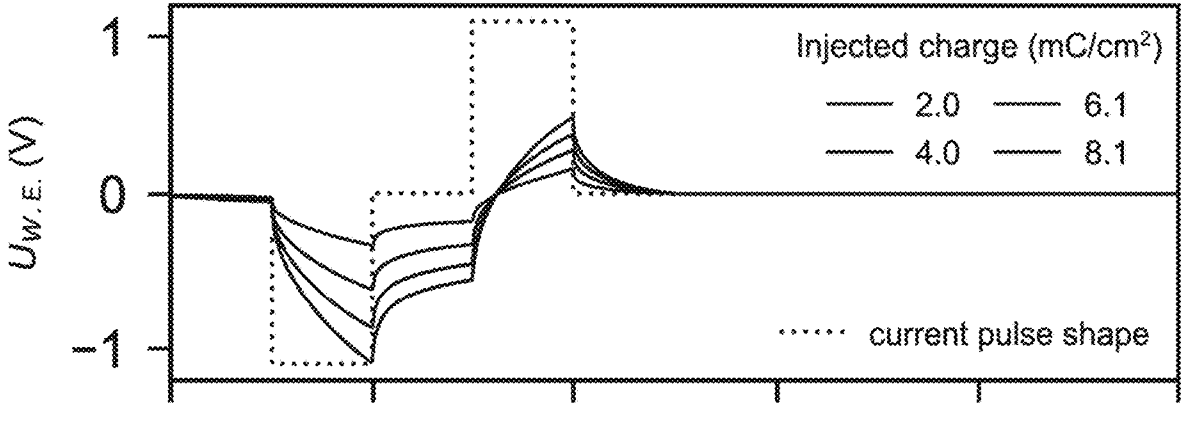
FIG. 20 a graph of the voltage response to current-controlled biphasic pulses of 1 ms/phase applied through a HTrGO structure electrodes according to the present invention.

To achieve safe stimulation of the nervous tissue, the voltage drop at the electrode-electrolyte interface should always remain within the potential window set by the CV in which no faradaic reactions occur. FIG. 20 shows the potential excursion that a 25 μm diameter HTrGO structure microelectrode experiences upon the injection of rectangular, biphasic current pulses (1 ms/phase) at charge densities of 2.0, 4.0, 6.1, and 8.1 mC/cm$^2$. A linear voltage shift of maximum 0.9 V exists between the ohmic drops at the edges of the pulses, indicating a capacitive-like behavior of the electrode-electrolyte interface within the limits of the potential window.

Figure 21:
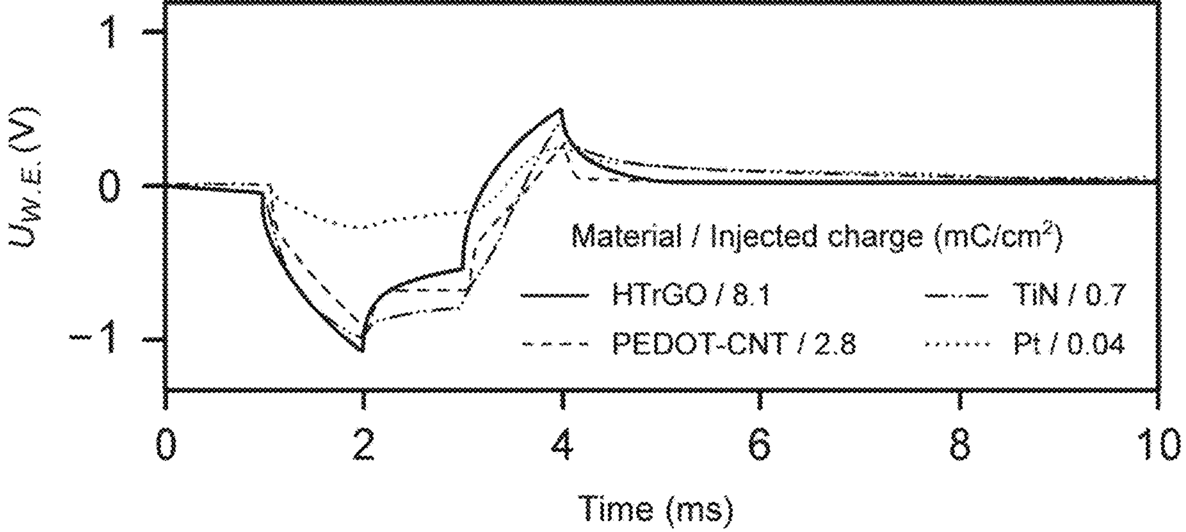
FIG. 21 a graph of the voltage response within the potential window of different materials as a response to injected currents of different amplitudes.

FIG. 21 compares the CIL of the HTrGO structure with that of CAEs. The CILs were measured at 2.8 mC/cm$^2$ for PEDOT-CNT, 0.7 mC/cm$^2$ for TiN, and 0.04 mC/cm$^2$ for Pt, each of which is significantly lower than the 8.1 mC/cm$^2$ measured for the HTrGO structure.

Figure 22:
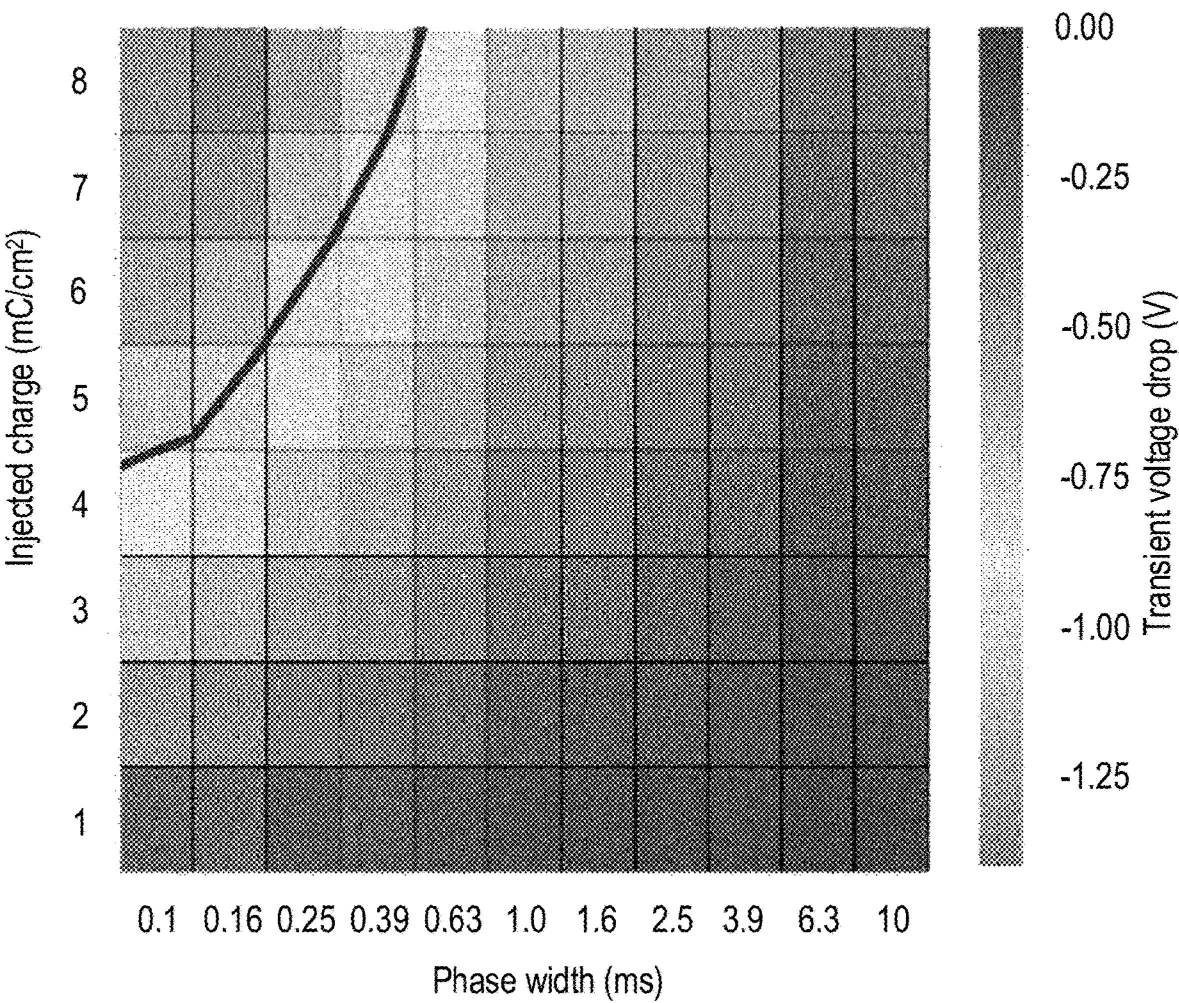
FIG. 22 a map of the cathodic voltage excursion occurred at the interface between HTrGO structure microelectrodes and the electrolyte during the injection of current pulses at different levels of injected charge and pulse widths.

FIG. 22 shows a map of the voltage polarization experienced by a HTrGO structure microelectrode in response to biphasic current pulses between 0.1 ms and 10 ms and injected charge densities up to 8.1 mC/cm$^2$. The pixels in the map below the purple line are the pulses whose parameters allowed the potential to remain within the electrochemical potential window. For short pulses of 0.1 ms, only 4 mC/cm$^2$ could be safely injected since the volumetric capacitance of the electrode could not be fully charged, whereas pulses longer than 1 ms could inject 8.1 mC/cm$^2$.

Figure 23:
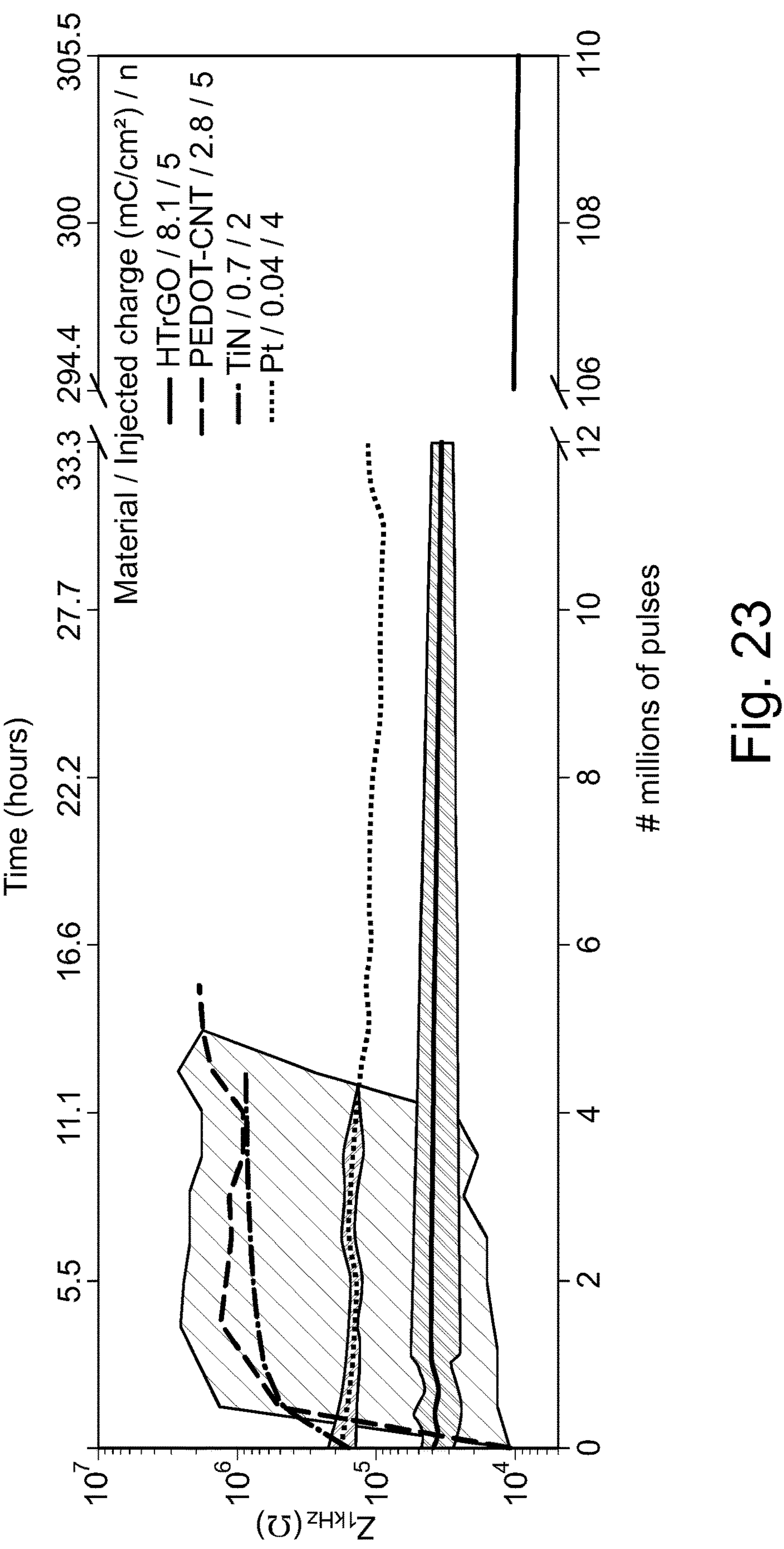
FIG. 23 a graph displaying the run of the impedance at 1 KHz measured with HTrGO structure electrodes and CAEs over continuous stimulation with biphasic pulses of 1 ms/phase.

To begin assessing the long-term neural interfacing potential of the microelectrode technology, the stability of the electrodes was investigated during continuous electrical stimulation, as presented in FIG. 23. The HTrGO structure microelectrodes and CAEs were stimulated at 100 Hz using their corresponding safety-limited current pulses shown in FIG. 21 and their impedance was periodically monitored. The standard value of >1 MΩ at 1 KHz impedance was used as indicator of severe electrode degradation. The HTrGO structure microelectrodes maintained a minimal impedance deviation after 110 million pulses, drastically outperforming PEDOT-CNT and TiN, which both degraded after 5 million pulses. While the Pt was able to maintain a minimal impedance deviation after 10 million pulses, its CIL is only 0.04 mC/cm$^2$ whereas the HTrGO structure electrodes have a CIL of 8.1 mC/cm$^2$ that is 200 times higher. The unique combination of high performance and high stability provided by the HTrGO structure is attributed to the fusion of the capacitive interaction in aqueous media with the large electrochemical surface area obtained during the hydrothermal reduction.

Recording Neural Signals

Figure 24:
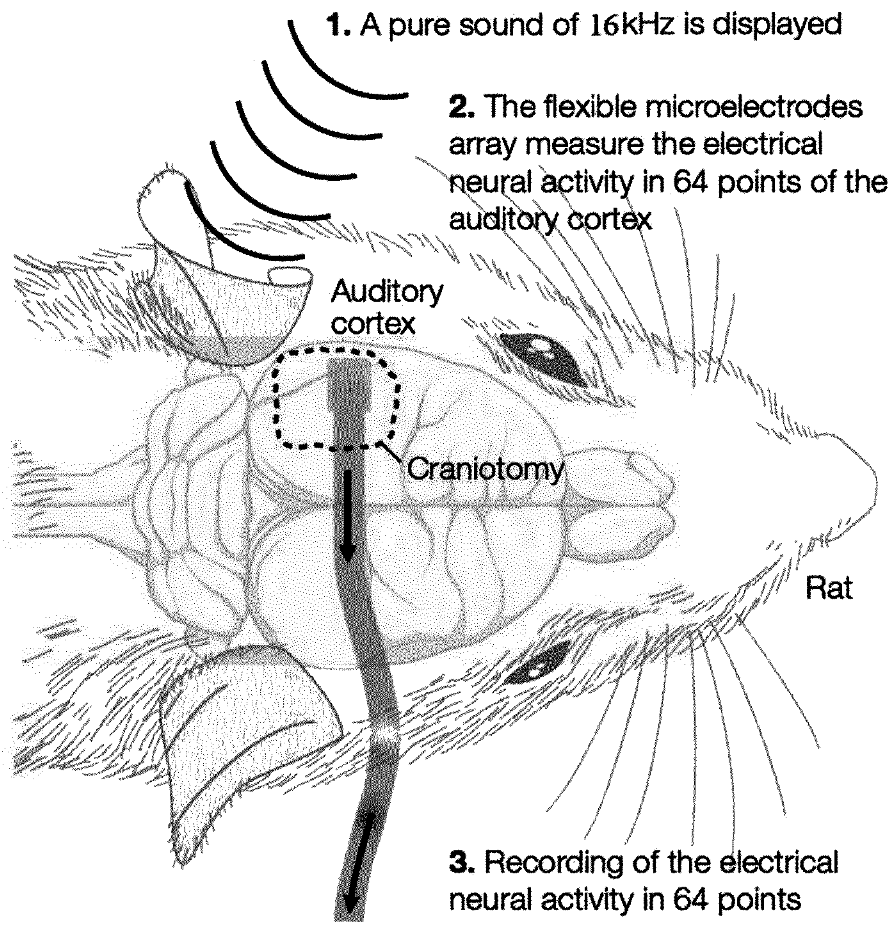
FIG. 24 a schematic diagram of the acute experiment using an HTrGO structure micro-electrocorticography (μECoG) flexible array to record epicortical neural activity of a rat.
Figure 25:
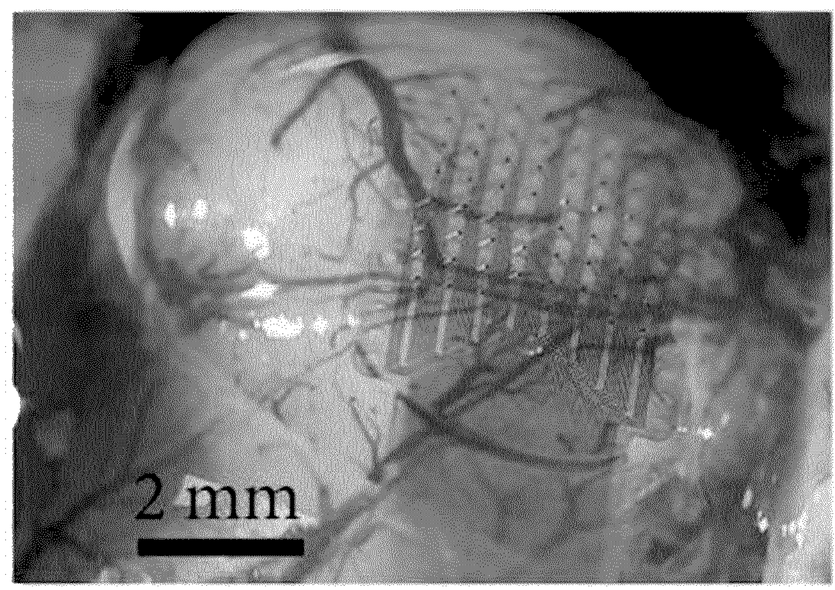
FIG. 25 a picture of HTrGO structure μECoG array on the auditory cortex of a rat.

The suitability of the HTrGO structure microelectrode technology to record in vivo neural signals was assessed by using flexible micro-electrocorticography (μECoG) HTrGO structure devices (cf. FIG. 10*b*) to monitor the neural activity at the surface of the auditory cortex of anesthetised Sprague Dawley rats (4-months old) (FIG. 24). The μECoG devices consist of arrays of 64 HTrGO structure microelectrodes (ø 25 μm, pitch 300 μm). The probe was positioned over the left auditory cortex (AI and AAF regions) (cf. FIG. 25).

Figure 26:
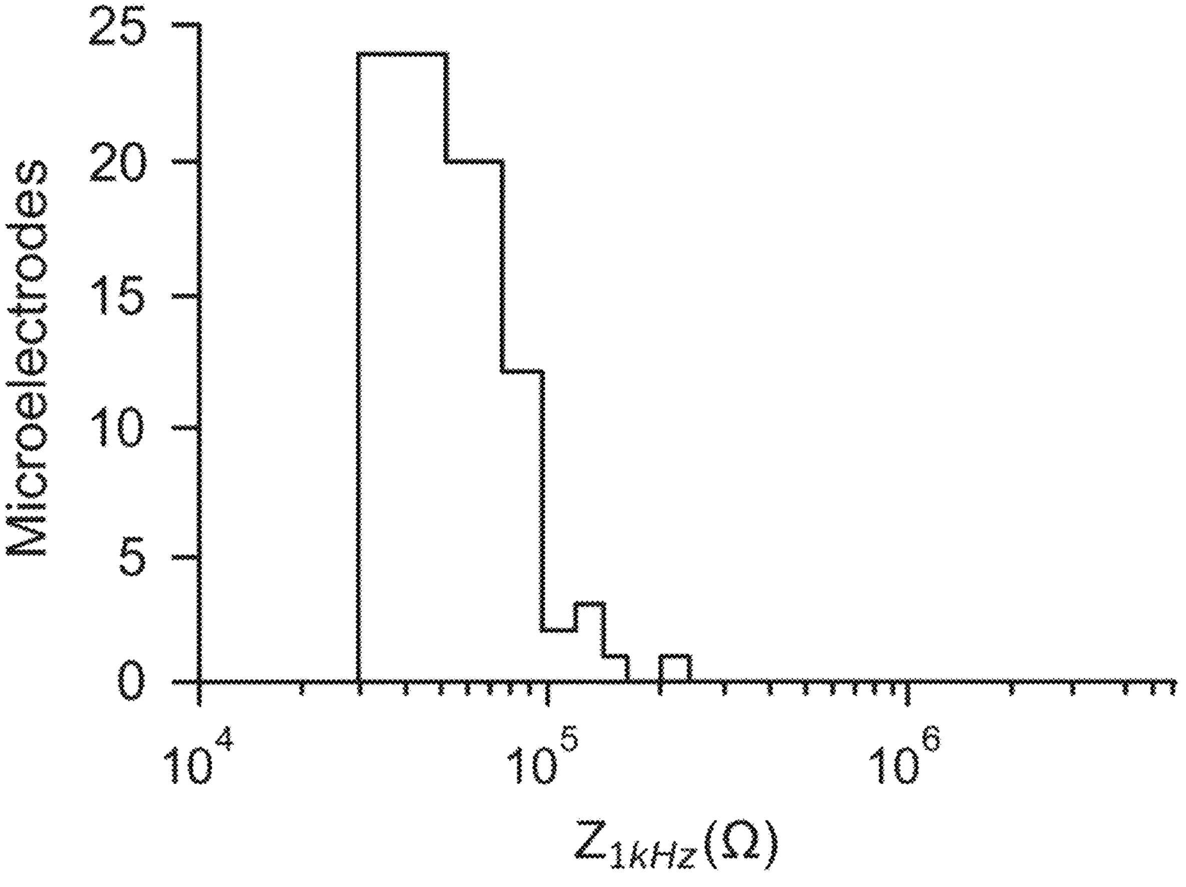
FIG. 26 a graph of the impedances at 1 KHz before implantation of HTrGO structure μECoG devices.

The average impedance of the microelectrodes was 58±25 kΩ at 1 KHz, as shown in FIG. 26. Pure tones of 16 kHz and 200 ms duration (3 ms rise and 20 ms fall times) were presented at 90 dB SPL to generate evoked activity.

Figure 27:
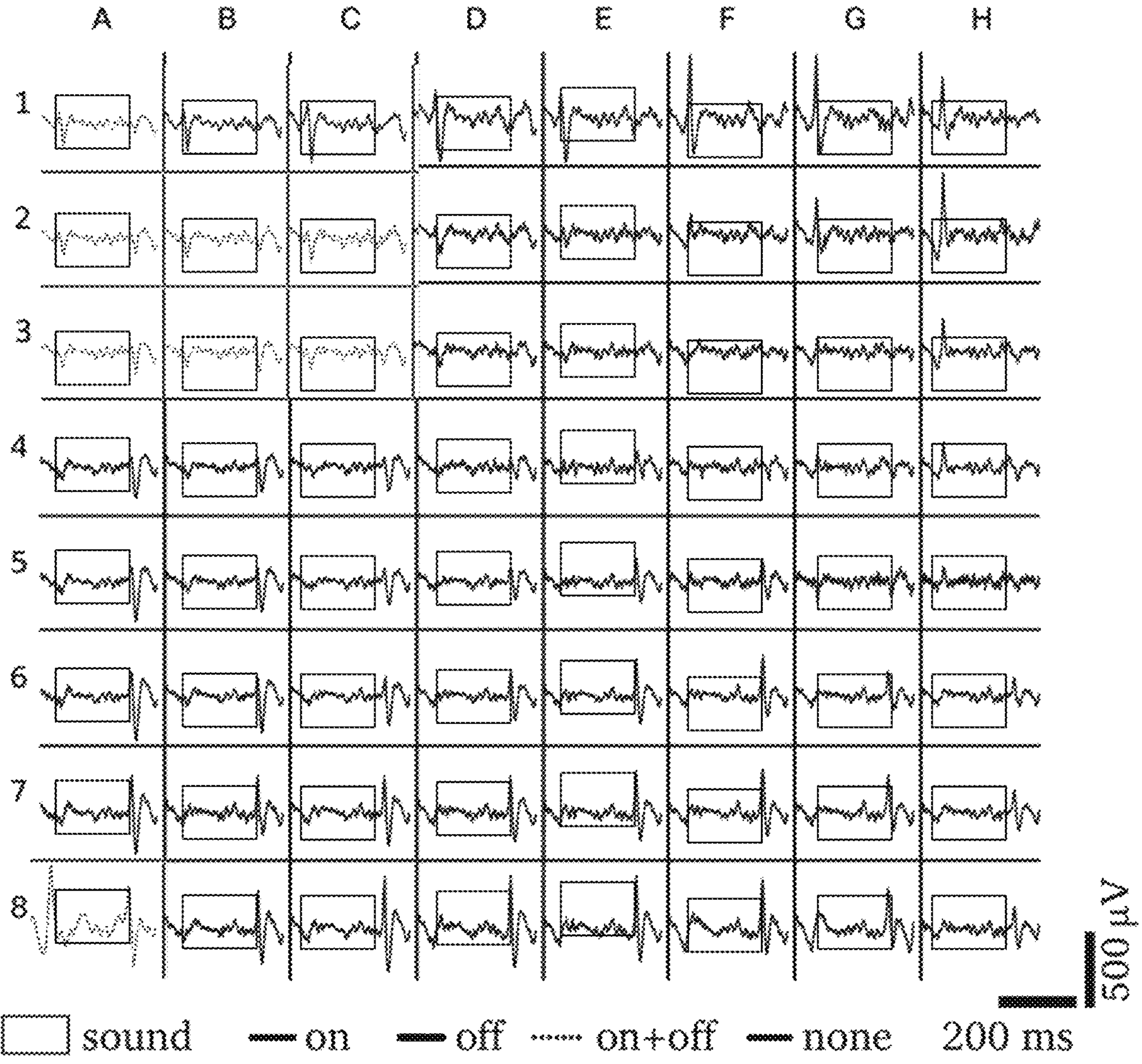
FIG. 27 a mapping of the evoked neural activity depicting a single event across all 64 HTrGO structure microelectrodes.

FIG. 27 shows the 10 Hz high-pass filtered signal from each of the 64 HTrGO structure electrodes in the array over a 350 ms window in which a pure tone was presented. The large negative and positive voltage peaks are observed after the onset and offset of the sound stimulus indicate the existence of evoked local field potentials (LFP). The high quality of the recorded signal allows mapping of single-event eLFPs as displayed in FIG. 27, which reveals a spatial clustering with ON responses (B1-H1, C2-H2, G3-H3, H4) located on the top right corner and OFF responses (A4-E4, A5-F5, A6-H6, A7-H7, B8-H8) grouped in the bottom region. The spatial distribution of ON and OFF responses (A1, A2-B2, A3-C3, A8) recorded during single events can vary from event to event.

Figure 28:
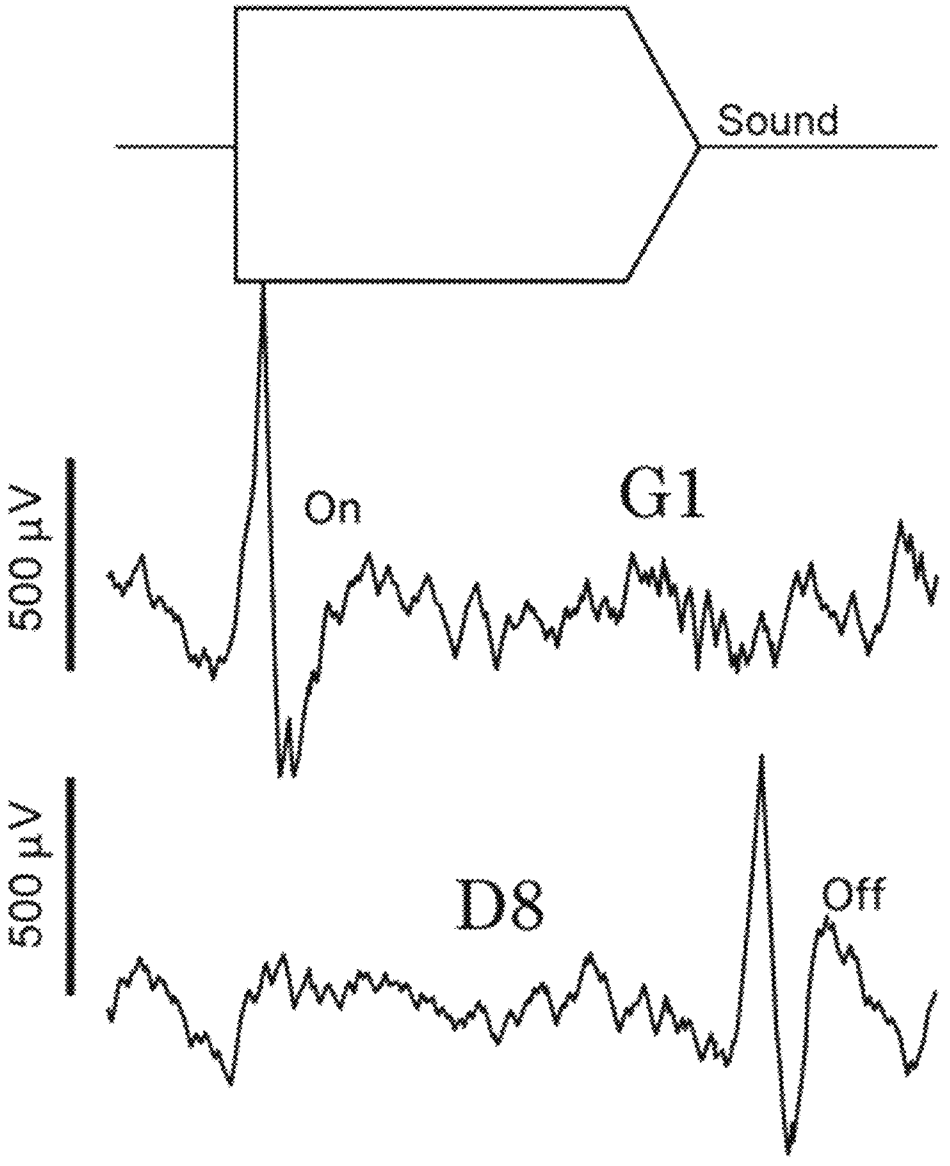
FIG. 28 a graph of the response of regions G1 (onset) and D8 (offset) to the evoked local field potentials according to FIG. 27.

FIG. 28 shows details of the ON and OFF single trial signals recorded in the two main clusters, extracted from regions G1 and D8 of the device (as indicated in FIG. 27), respectively. The amplitudes of the evoked response range between 500 μV and 700 μV. Typically, the ON signals are observed 30 ms after the onset of the sound stimulus, while the OFF signals are observed 34 ms after the offset of the stimulus. These latencies are in good agreement with previous reports41.

Figure 29:
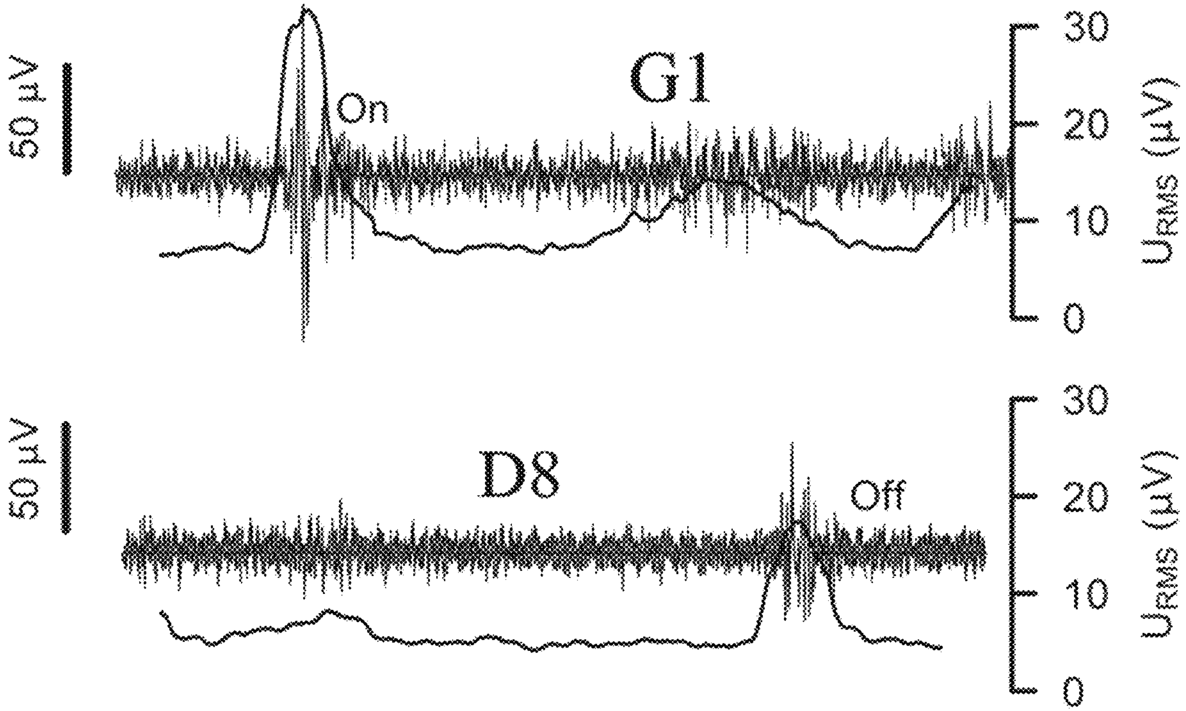
FIG. 29 the graph of FIG. 28 high-pass filtered at 200 Hz to reveal high frequency MUA activity.
Figure 30:
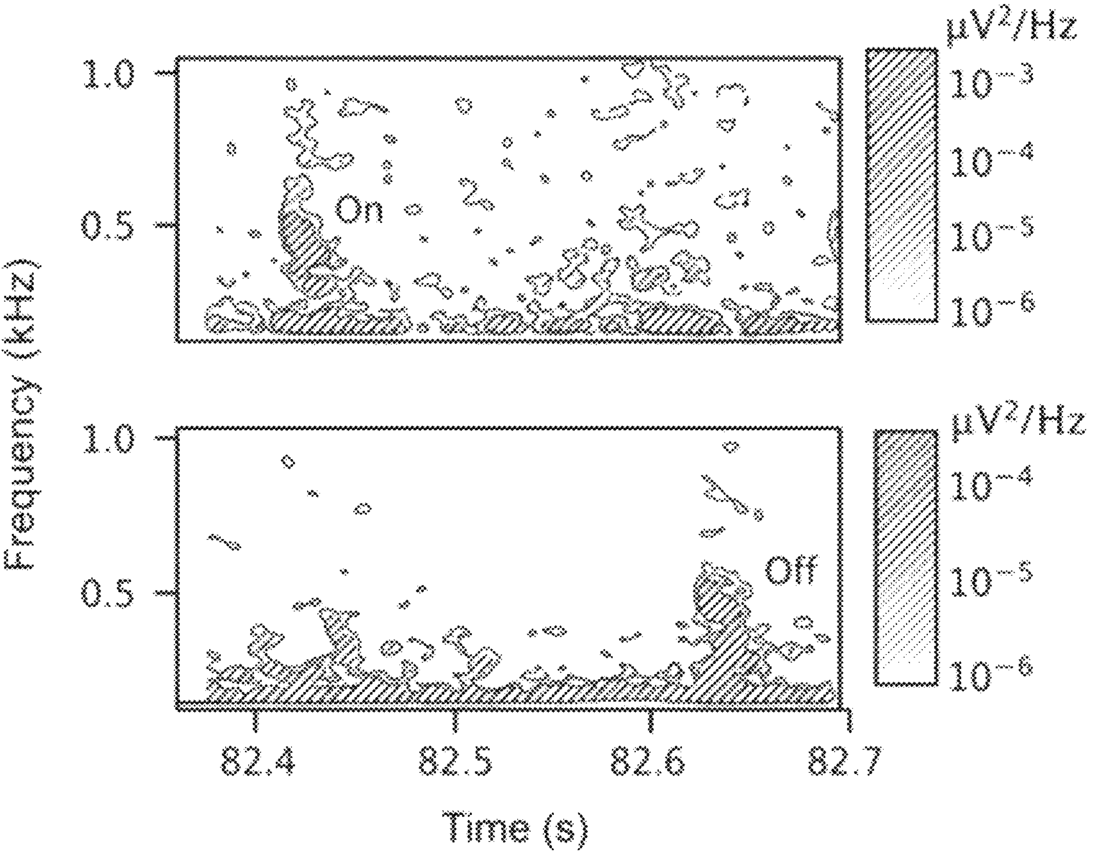
FIG. 30 a spectrogram of the neural activity measured at G1 and D8 of FIG. 27 during activation and deactivation of the auditory signal.

FIG. 29 shows the same signals from regions G1 and D8 high-pass filtered at 200 Hz overlapped with its root mean square (RMS) value. The high frequency multi-unit activity (MUA) and the corresponding increase of the RMS amplitude due to MUA nicely correlate to the eLFP, indicating a synchronous behavior of the neurons to the stimulus41. The spectrograms of the electrical recordings of G1 and D8 (cf. FIG. 30) confirm the increase of high frequency neural activity at the stimulation onset and offset.

Figure 31:
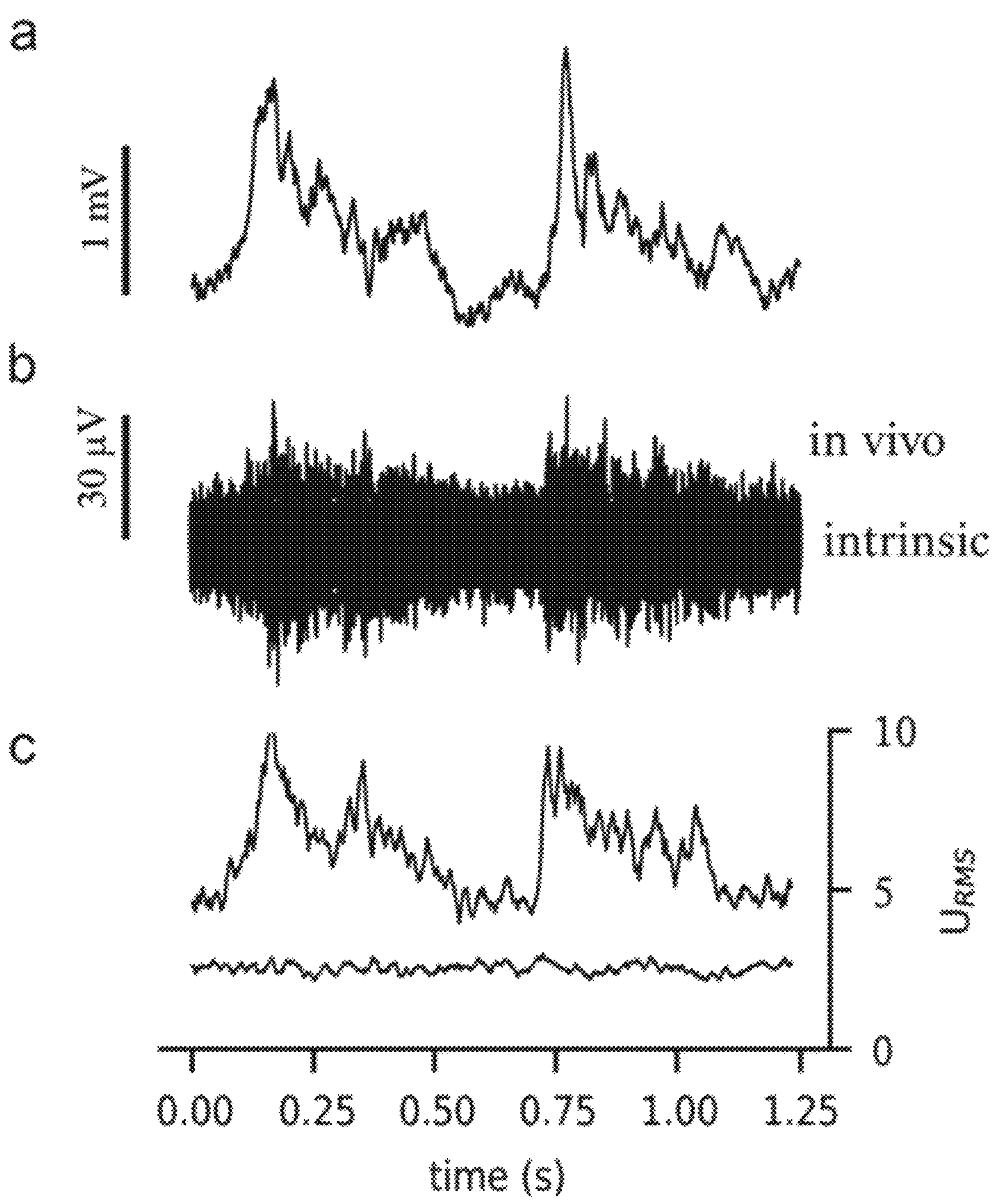
FIG. 31 signal graphs of spontaneous activity recorded with HTrGO structure microelectrodes.

The recording capability of HTrGO structure microelectrodes is further confirmed in recordings of spontaneous cortical activity, as presented in FIG. 31*a*. The amplitude of the recorded spontaneous activity exceeds that of the evoked signal due to the contribution of the signals below 10 Hz. The high-pass filtering of the signal at 200 Hz shown in FIG. 31*b* uncovers the contribution of low-amplitude (20-30 μV peak-peak), high frequency components of the signal, which are found to disappear post-mortem. The calculation of the RMS noise of the signals allows correlation of the low and high frequency components of the spontaneous activity. The intrinsic RMS noise of the electrode (calculated from the post-mortem recordings) was of 2.5 μV, which was very close to the technical capabilities of the electronic setup.

Figure 32:
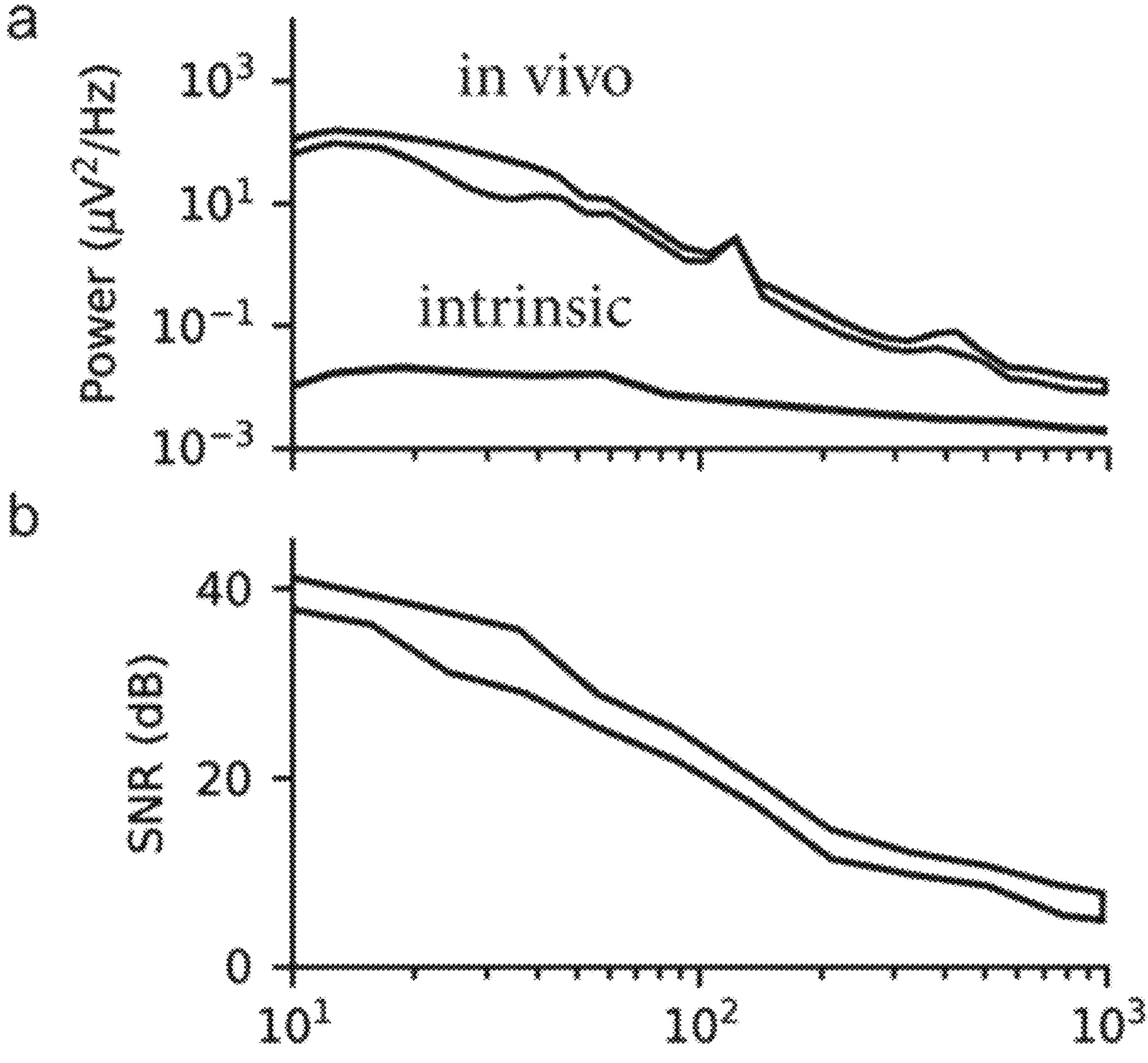
FIG. 32 a graph of the power spectral density (PSD) of the HTrGO structure microelectrodes, in in vivo (top) and post-mortem (bottom) conditions.

FIG. 32*a* shows the averaged power spectral density (PSD) obtained from 60 HTrGO structure electrodes over a 30-minute in vivo recording, compared to the PSD of a post-mortem recording. The SNR (calculated from the division of the signals) reaches 40 dB at 10 Hz and 5 dB at 1 kHz, as shown in FIG. 32*b*, demonstrating an excellent capability to record high fidelity signals at both low and high frequencies.

To benchmark the recording capabilities, similar measurements were performed using a CAE of Pt (ø 60 μm, NeuroNexus). The average electrode impedance was 695±361 kΩ, which is one order of magnitude larger than the 25 μm diameter HTrGO structure microelectrodes. Evoked and spontaneous signals of lower amplitude were recorded with Pt electrodes and the calculated SNR was 25 dB at 10 Hz and 2 dB at 1 KHz. The Pt electrodes were outperformed by a factor of 2 by the HTrGO structure microelectrode technology.

Stimulation of Nerve Fibres

Figure 33:
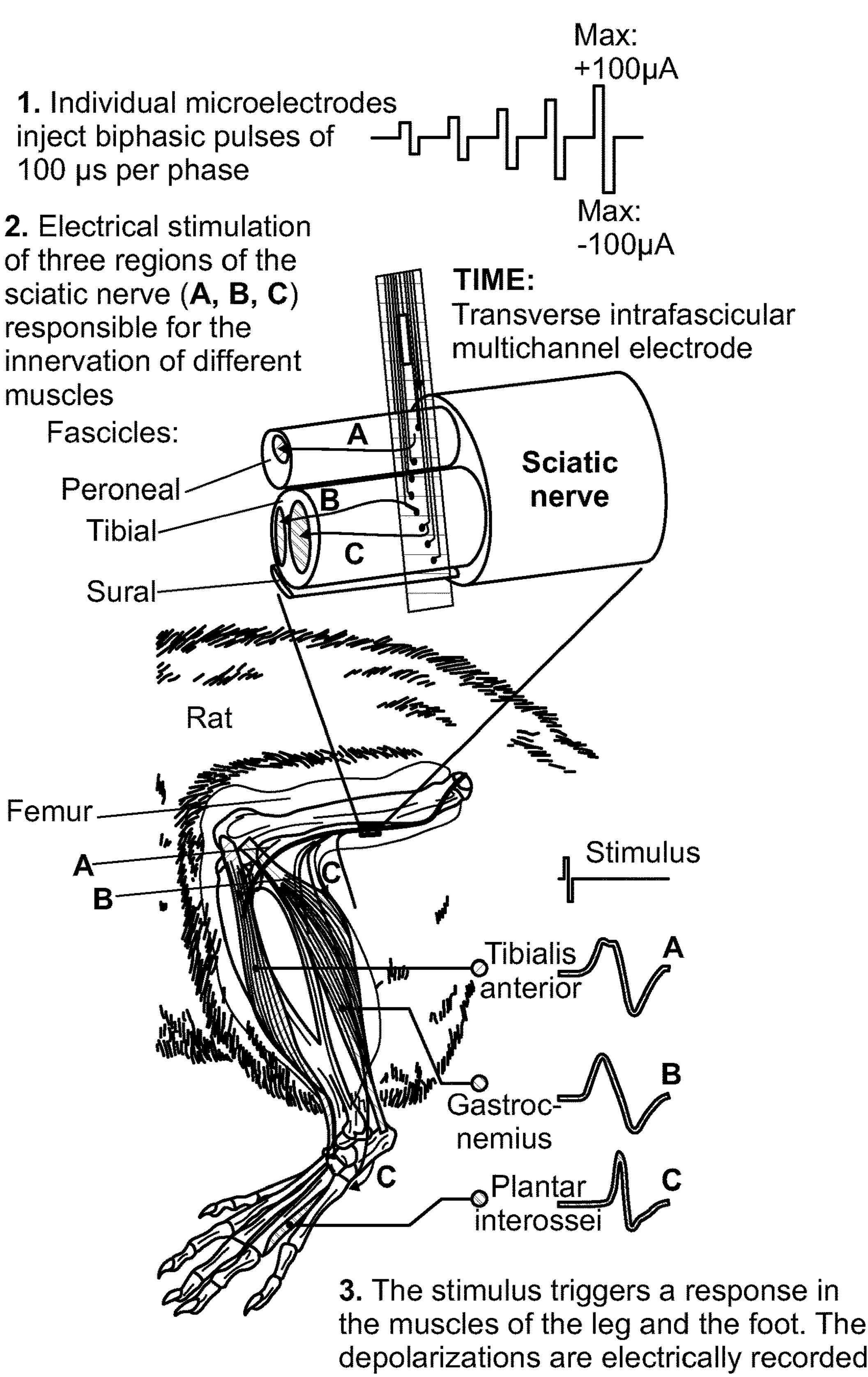
FIG. 33 a schematic diagram of the acute stimulation experiment.

In order to evaluate the stimulation capability of the HTrGO structure microelectrodes, devices inspired by the transverse intrafascicular multichannel electrode (TIME) were implanted transversally in the sciatic nerve of anesthetised Sprague Dawley rats in acute experiments, as presented in FIG. 33.

In a similar way with respective necessary adaption in e.g. size of the electrode device, this can be also done in mammals and in humans.

Figure 34:
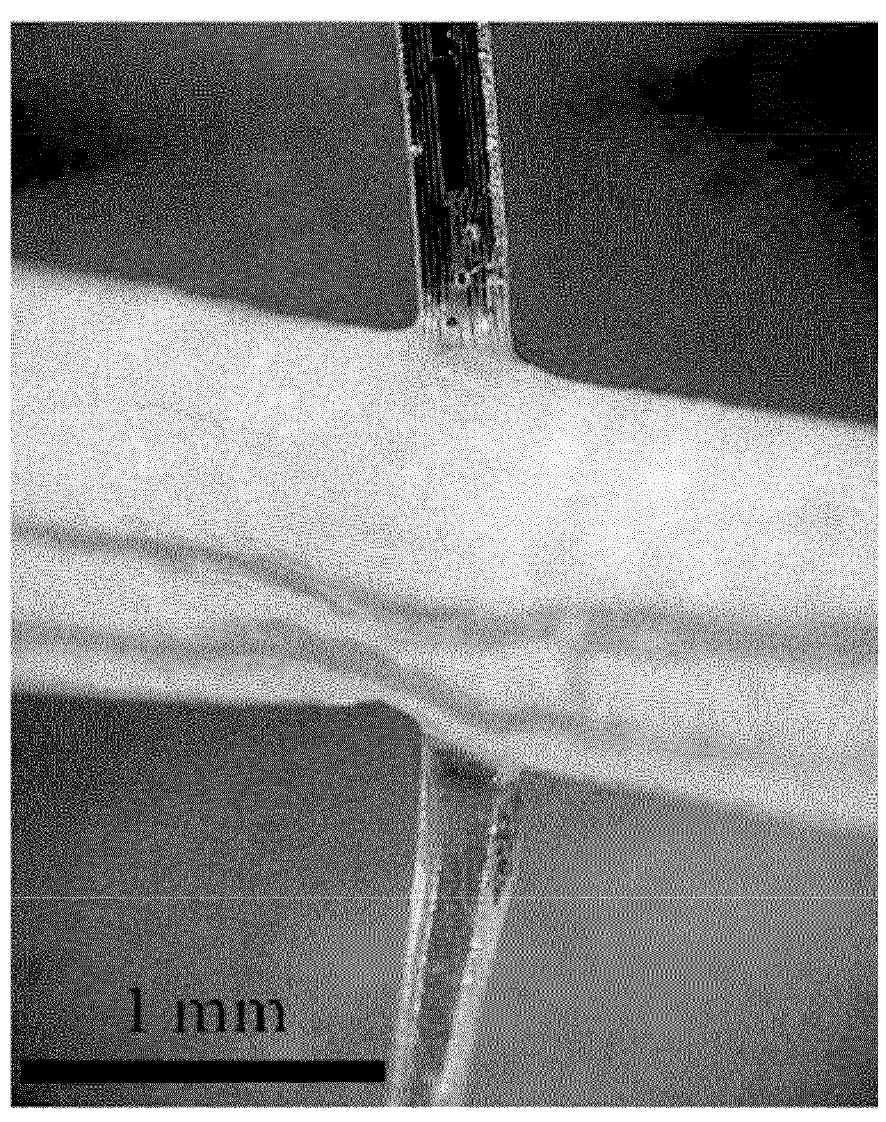
FIG. 34 an optical micrograph of the implanted transverse intrafascicular multichannel electrode (TIME) device in the sciatic nerve.
Figure 35:
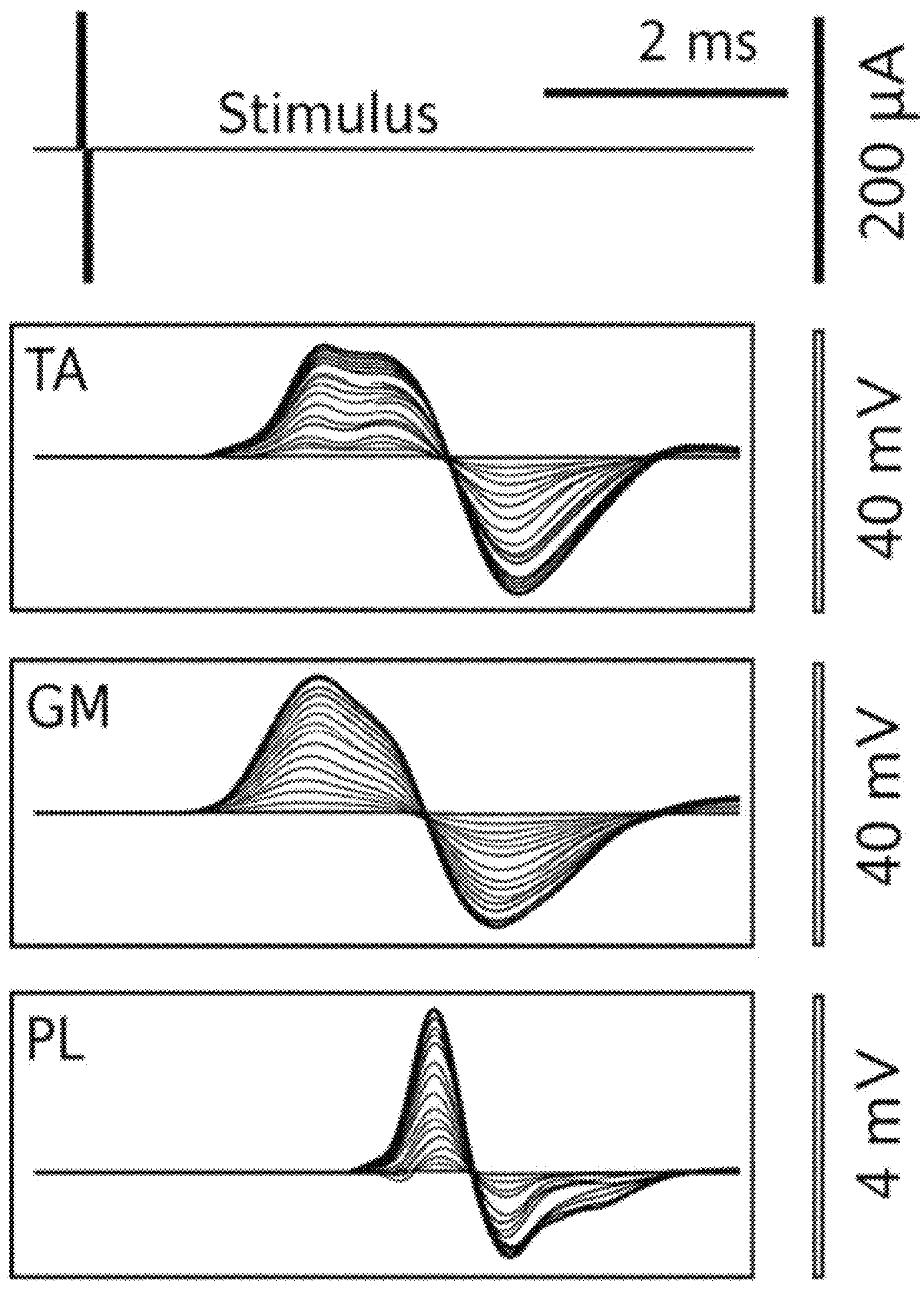
FIG. 35 a graph of measured compound muscle action potentials (CMAPs) recorded from the tibialis anterior (TA), gastrocnemius (GM), and plantar interosseous (PL) muscles in response to increasing levels of injected current pulses applied to one of the electrodes FIG. 36 recorded CMAP in TA, GM, and PL muscles in response to trains of biphasic current pulses of increasing amplitude applied to the 9 microelectrodes of the array A, at one side of the TIME.

The device consisted of 2 linear arrays (A and B) of 9 electrodes (ø 25 μm) along a 1.2 mm stripe. Each linear array faced opposite sides of the stripe. Once implanted, as presented in FIG. 34, the device crossed the peroneal fascicle (responsible for the innervation of the tibialis anterior (TA) muscle) and the tibial fascicle (responsible for the innervation of both the gastrocnemius (GM) and plantar interosseous (PL) muscles). Each electrode in the HTrGO structure array was individually stimulated and the elicited compound muscle action potentials (CMAP) of the TA, GM, and PL muscles were simultaneously recorded by monopolar needles inserted in the muscles (cf. FIG. 35).

Figure 36:
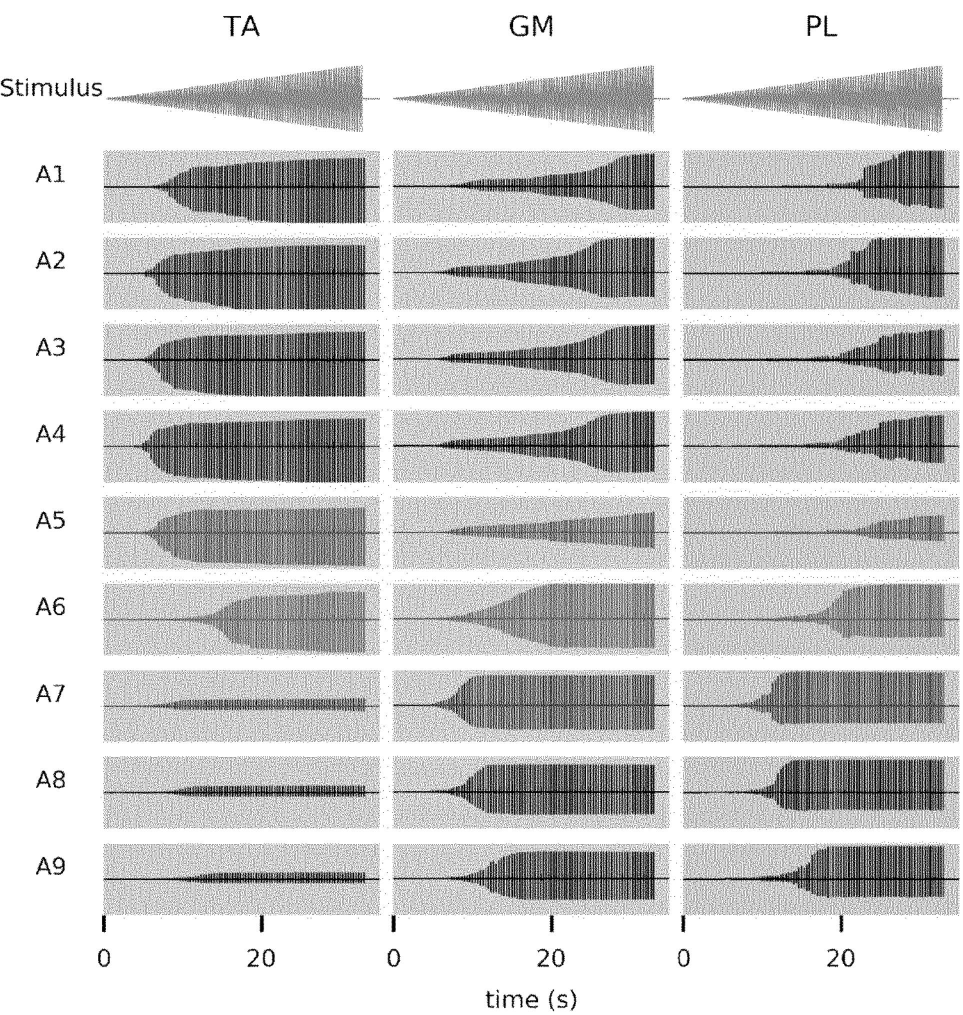
Figure 37:
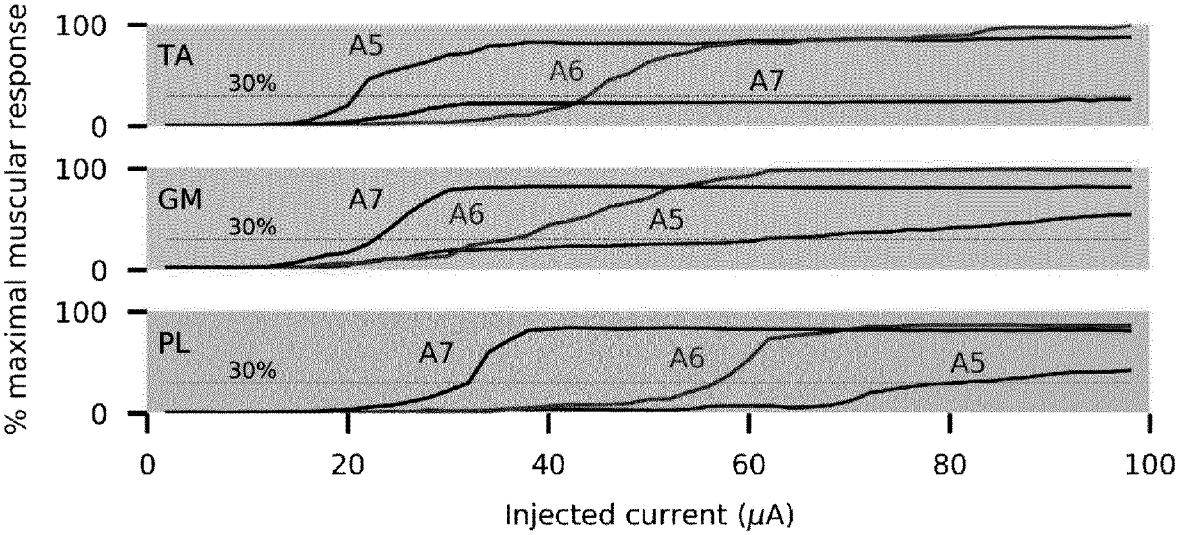
FIG. 37 normalized CMAP of TA, GM, and PL muscles in response to pulses injected to microelectrodes A5-A7 of FIG. 36 from the implanted TIME.

To stimulate the nerve, a train of 100 biphasic pulses (100 μs/phase) with increasing current amplitude (0 to 100 μA, in 1 μA steps) were injected through the microelectrodes at 3 Hz for 33 seconds. FIG. 36 shows the recorded response of TA, GM and PL muscles to these current pulses applied through the A1-A9 microelectrodes. The recorded signals are normalized to the maximum amplitude of the CMAP. The first recorded CMAP appeared in response to low intensity stimulation of about 15-20 μA and then showed a fast increase in amplitude until a maximum activation was reached. The recruitment curves reflect the typical sigmoidal shape, as shown in FIG. 37. The pattern of muscular activation changed depending on the stimulating electrode. The activity could be split in 2 clusters: one for A1-A5, in which the TA muscle was activated at lower stimulus intensity than the GM and the PL muscles, and another one for A7-A9, in which the GM and PL muscles exhibited more activity than the TA muscle. This suggests that the first five microelectrodes were placed in the peroneal fascicle, whereas the last three were located within the tibial fascicle. From these responses, critical parameters for implants aiming at restoring mobility such as current thresholds and selectivity index of the modulated the muscular activity can be derived.

Of particular interest are electrodes A5-A7, which are located nearest the interface between the two peroneal and tibial fascicles. In these electrodes, significant changes of current threshold and selectivity index were observed. Using 30% of muscle activation (the minimum stipulated to overcome gravity) as a benchmark, the current stimulation at which this occurred for each muscle was determined. The pulse current needed for evoking a CMAP of 30% the maximal amplitude in the TA muscle was 21 μA when stimulated by A5, 45 μA by A6, and could not be achieved by A7 (cf. FIG. 37). For the PL muscle the current was 33 μA when activated by A7, 45 μA by A6 and 81 μA by A5. Similarly, GM muscle required 23 μA when activated by A7, 37 μA by A6 and 62 μA by A5. From these data, a selectivity index above 0.85 was calculated for the 30% activation of the TA, 0.77 for the GM, while for the PL it was only 0.44. As an indicator, an optimal selectivity index of 1 indicates that one muscle can be solely activated without any activation in the other recorded muscles. Taking into account that the TA innervation is conveyed through the peroneal fascicle and the innervations of the GM and the PL are contained in the tibial fascicle, the lower activation thresholds and higher selectivity indices are obtained for stimuli coming through electrodes placed in closer positions. Therefore, it can be derived that A5 is located within the peroneal fascicle, A7 in the tibial fascicle, and A6 is likely between the two fascicles. The lower selectivity index obtained by the PL is probably due to the high dispersion of the nerve fibers innervating this muscle within the tibial fascicle compared to the more confined fibers of the TA and GM.

Figure 38:
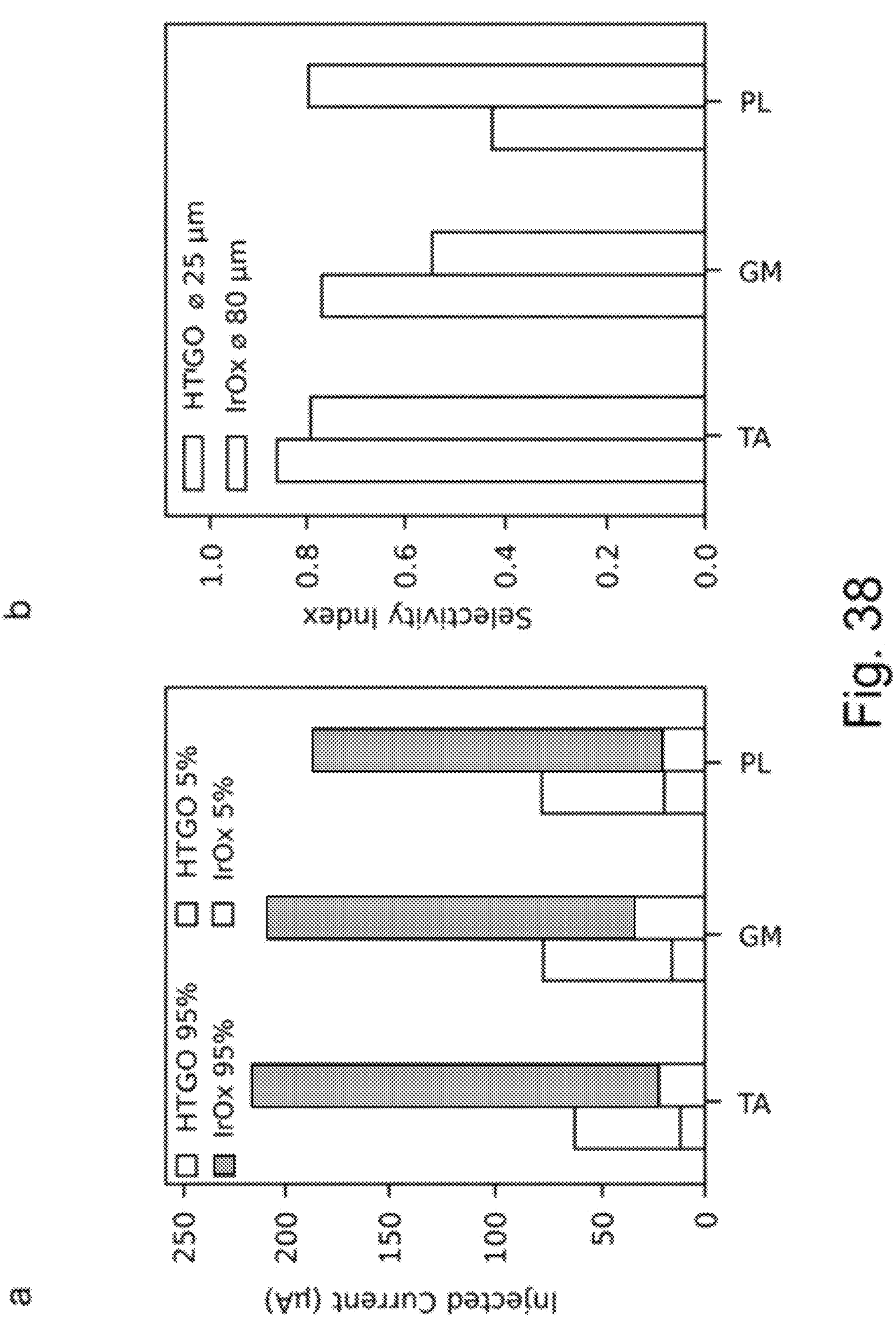
FIG. 38*a, b* a) a comparative plot of the injected current needed to elicit a 5% and 95% of the maximum CMAP using microelectrodes for the HTrGO structure (left bars) and IrOx46 (right bars) and b) a comparative plot of the selectivity index at the minimal functionally relevant muscular stimulation for HTrGO structure (left bars) and IrOx (right bars)

FIG. 38*a* shows the minimum current thresholds to achieve a 5% and a 95% of the CMAP amplitude in TA, GM and PL muscles taking into account the activity triggered by all the microelectrodes shown in FIG. 36. To reach 5% contraction, less than 50 μA were required for all the muscles, whereas less than 100 μA were needed to reach 95% of maximal activity. Compared to previous studies in which TIMES arrays with five 80 μm diameter electrodes of iridium oxide were used, HTrGO structure electrodes elicited a response with thresholds 2 to 3 times lower. The selectivity index values achieved with HTrGO structure electrodes also improved with respect to those previously obtained using larger IrOx electrodes, indicating higher focality in the stimulation (cf. FIG. 38*b*).

Thus, the high charge injection limit of the HTrGO structure allows the fabrication of smaller electrodes while maintaining neural stimulation capabilities. As a result, the injected current is highly focalized into nearby regions, permitting a higher resolution and more efficient electrical stimulation of the highly confined TA and GM nerve fibers.

Apart from the therapeutic advantage this can provide, the power consumed by the stimulation device can be significantly reduced and its functional lifetime can be extended, even after fibrotic encapsulation (cf. FIG. 38*b*).

Chronic In Vivo Biocompatibility Studies

To assess the biocompatibility of a thin-film HTrGO structure devices, chronic biocompatibility studies with epicortical and intraneural implants were carried out.

Figure 39:
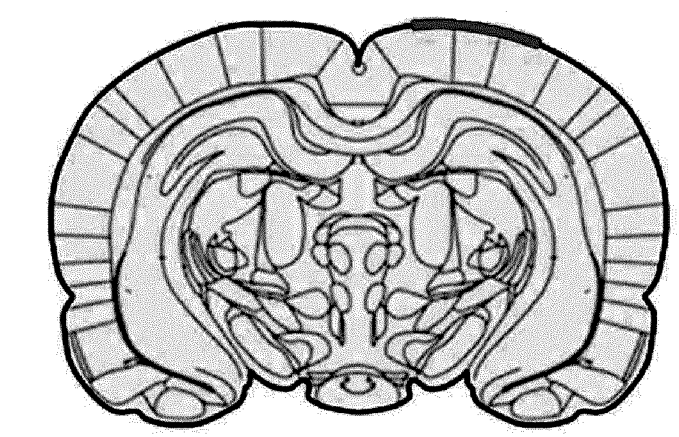
FIG. 39 a diagrammatic representation of the HTrGO structure device implant location is demonstrated by the bold line on coronal (top) and sagittal (bottom) rat brain sections.
Figure 39:
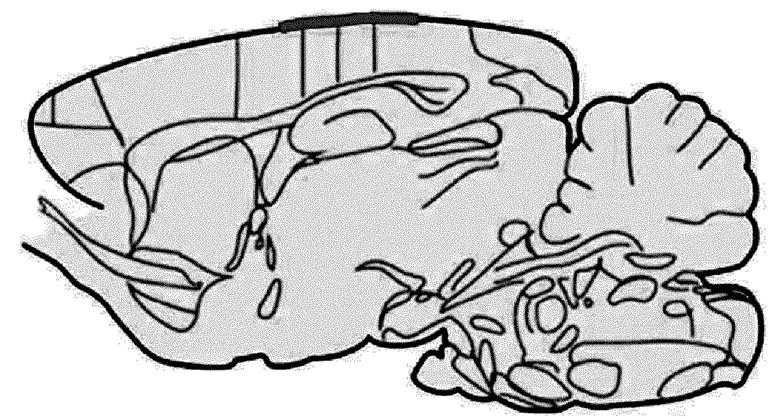
Figure 40:
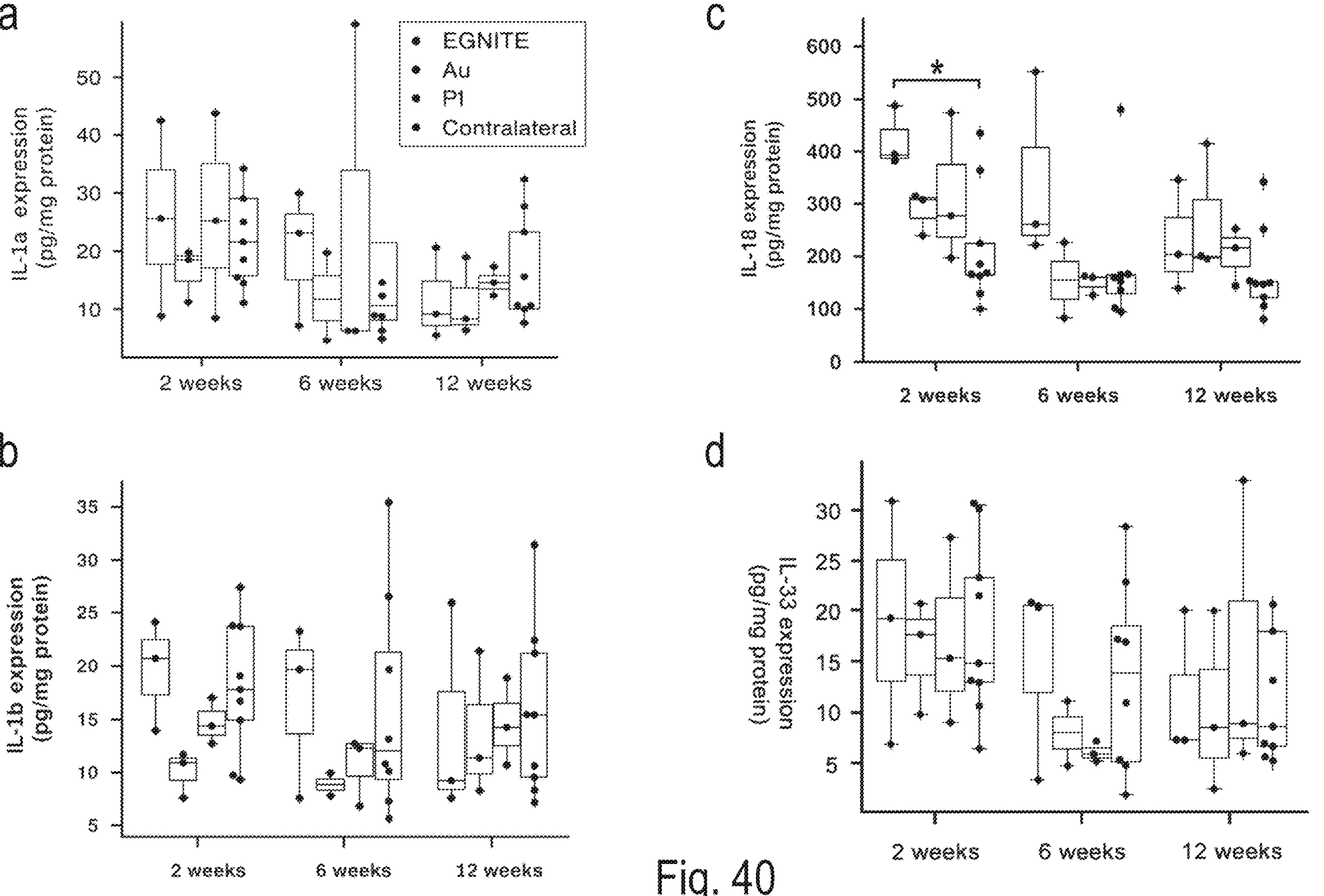
FIG. 40 plots of microglial activation in the cortical region underneath the probe site.

A 12-week chronic biocompatibility study of epicortical implants was conducted to determine any neuro-inflammation caused by these devices. The epicortical devices were implanted on the right hemisphere of adult, male Sprague-Dawley rats (cf. FIG. 39*a, b*) for up to 12 weeks before extraction of cortical brain tissue for either ELISA or histological evaluation. Gold and Polyimide (PI) based implants were used to compare with the Graphene based HTrGO structure device at three timepoints; 2 weeks, 6 weeks and 12 weeks (n=3 per group). Immunohistochemical and cytokine analysis of brain tissue for inflammatory markers was performed and compared to the contralateral hemisphere (without device implantation).

Immunohistochemical analysis of the tissue demonstrates no significant change to the levels of inflammatory cytokines present in the brain at each timepoint, or with different device materials, as it can be derived from FIG. 40*a* to FIG. 40*d*. A slight increase in IL1b, IL-6 and MCP-1 can be seen in the 2 and 6 week HTrGO structure samples compared to those implanted with Gold or PI, however this difference is not seen at the 12 week time point and was not found to be significant (cf. FIG. 40*b*). When compared to the contralateral hemisphere at each timepoint, again no appreciable difference can be seen in any of the cytokines quantified, with the exception of the anti-inflammatory marker IL-18 (cf. FIG. 40*c*) which is significantly increased at 2 weeks following implantation with a HTrGO structure compared to the contralateral hemisphere. However, by 12 weeks this reaction was abated. Furthermore, Iba-1 staining of the brain tissue after device implantation was completed to assess the level of microglial cell activation in the region directly beneath the device implantation site. Similarly, the results of this show no significant difference in the levels of activation, regardless of device material or timepoint (cf. FIG. 40*a*). Together, the data presented suggests no increased or adverse neuro-inflammation is caused by the chronic implantation of HTrGO structure devices, and therefore highlighting their suitability for epicortical implantation.

Figure 41:
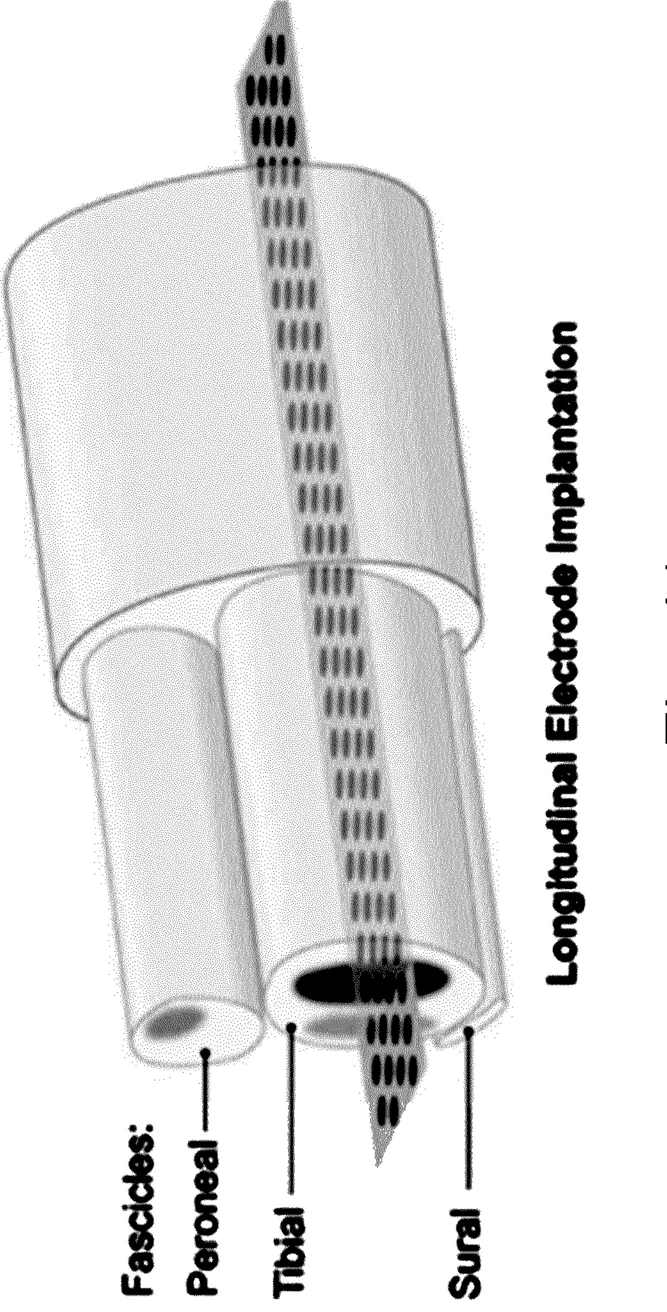
FIG. 41 a schematic diagram of the chronic in vivo biocompatibility experiment in which a polyimide device with and without many HTrGO structure dots is implanted in the tibial branch of the sciatic nerve of rats.
Figure 42:
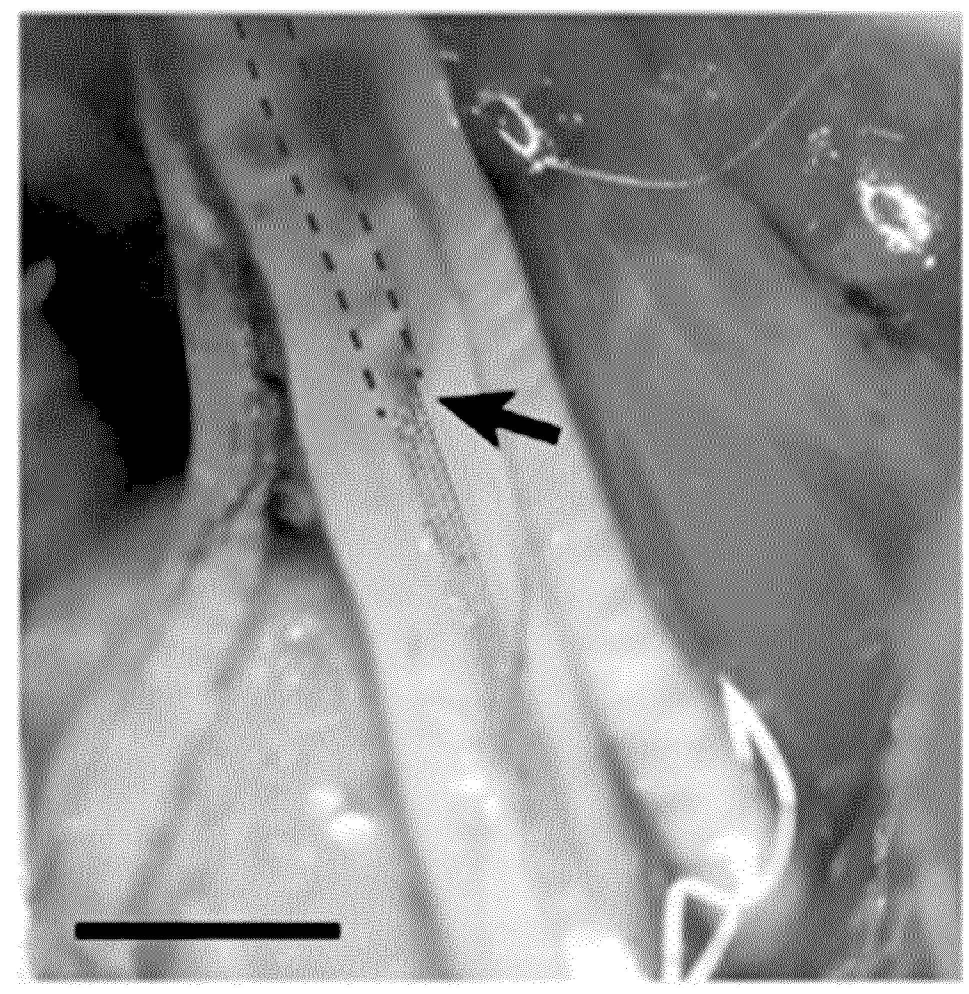
FIG. 42 an optical micrograph of the longitudinally implanted device for biocompatibility assessment in the rat sciatic nerve.

To study the biocompatibility of HTrGO structure devices in sciatic nerve, a special intraneural device, as shown in FIG. 41, was designed in which the area of HTrGO structure in contact with the nerve was increased by a factor of 9, aiming to maximize the contact area of the material with the tissue and to investigate immune responses. These intraneural implants, with and without HTrGO structure, were longitudinally implanted in the tibial branch of the sciatic nerve of Sprague-Dawley rats, as displayed in FIG. 42. Electrophysiological, pain and locomotion functional studies as well as immunohistochemical labelings of the nerve were conducted at 2 and 8 weeks post-implantation and compared to the contralateral nerve or paw (n=6-8 per group).

The results of nerve conduction tests did not show any difference in the CMAP amplitude and latency between the implanted paw with polyimide alone, with polyimide plus HTrGO structure or the contralateral paw during the 8 weeks follow-up, indicating that there was no damage to myelinated motor nerve fibers by any of the implants. The mechanical algesimetry test, typically used to assess pain, showed no changes between groups at any time point, indicating that there was no damage of small nerve fibers or irritation induced by nerve compression or axonal injury. Finally, the walking track test to assess locomotor function did not show variations between the two types of devices along follow-up, confirming that there was no functional nerve damage in the rats assessed.

Figure 43:
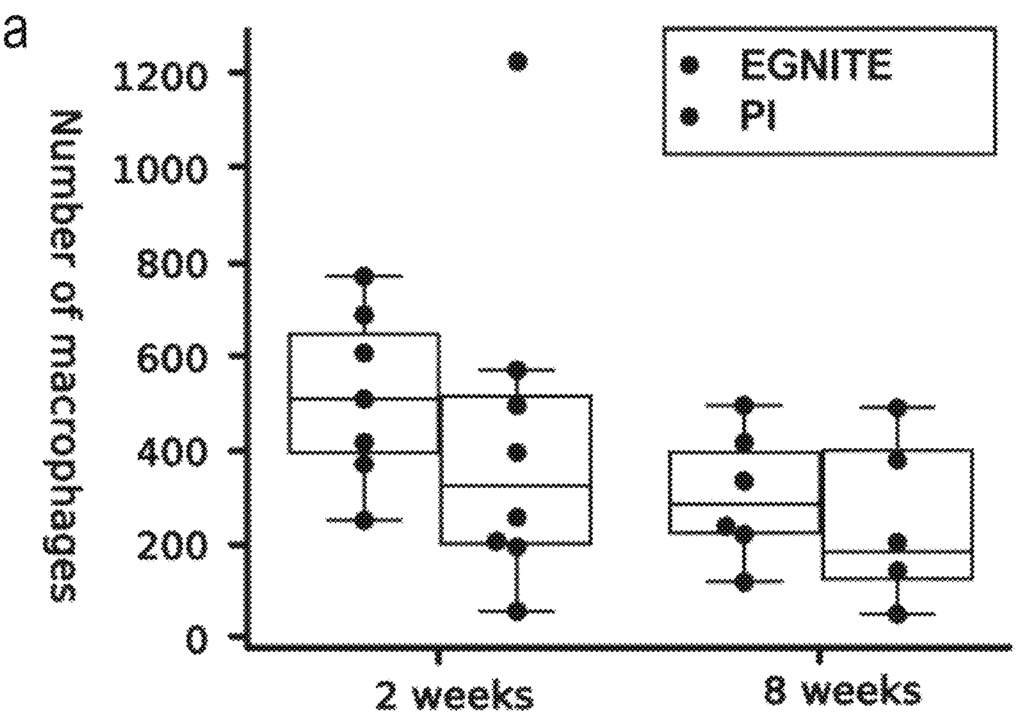
FIG. 43 a plot (top) of the tissue capsule thickness around the biocompatibility devices, with and without HTrGO structure, 2 and 8 weeks after the nerve implant and a plot (bottom) of the number of inflammatory Iba1+ cells in the tibial nerve of animals implanted in the same conditions than in the plot above.
Figure 43:
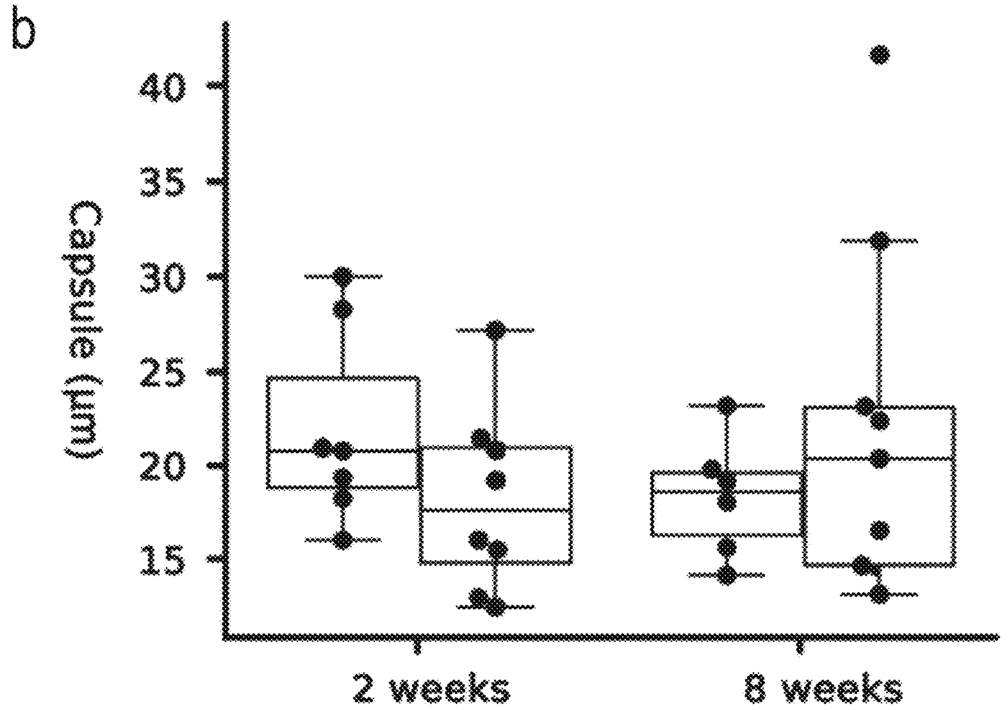

The histological analysis indicated that there were no signs of nerve damage or axonal degeneration induced by the implants. One of the main events during the foreign body reaction (FBR) is the infiltration by hematogenous macrophages into the implanted site, as part of the inflammatory phase. Comparison between implants with and without HTrGO structure revealed no differences in the amount of macrophages in the nerve as can be inferred from FIG. 43. The last phase of the FBR and one the main obstacles for long-term functionality of intraneural electrodes is the formation of a fibrous capsule around the implant. FIG. 43*b* shows that the capsule thickness was similar for implants with and without HTrGO structure at both 2 and 8 weeks, indicating that HTrGO structure does not induce damage to the nerve and fibrotic scar formation.

Immunohistochemical images, as shown in FIG. 44, show numerous axons near the implants (at around 20 μm) at both time points indicating limited damage and remodeling after implant. Altogether, the chronic biocompatibility study indicates that the HTrGO structure is suitable for chronic intraneural implantation, inducing no significant nerve damage nor neuroinflammatory response.

REFERENCE SIGNS

10 GO structure
12 GO layers
14 charged ions of an electrolyte system
20 HTrGO structure
22 HTrGO layers
24 charged ions of an electrolyte system
26 in-plane holes formed by hydrothermal reduction

The invention claimed is:

1. A reduced graphene oxide structure for stimulation and/or recording of the central and/or peripheral nervous system comprising a stack of layered, reduced graphene oxide flakes, wherein the reduced graphene oxide structure is obtainable by hydrothermal reduction and electrochemically activated in an electrolyte system.

2. The reduced graphene oxide structure for stimulation and/or recording of the central and/or peripheral nervous system according to claim 1, wherein the reduced graphene oxide structure comprises a plurality of holes having a diameter equal to or less than 10 nm.

3. The reduced graphene oxide structure for stimulation and/or recording of the central and/or peripheral nervous system according to claim 2, wherein the plurality of holes are permeable for charged ions.

4. The reduced oxide structure for stimulation and/or recording of the central and/or peripheral nervous system according to claim 3, wherein the charged ions are arranged between the layers of the reduced graphene oxide flakes and on the outer surfaces of the stack.

5. The reduced graphene oxide structure for stimulation and/or recording of the central and/or peripheral nervous system according to claim 1, wherein the distance between two consecutive layers of the reduced graphene oxide flakes is between 0.2 nm and 0.7 nm.

6. The reduced graphene oxide structure for stimulation and/or recording of the central and/or peripheral nervous system according to claim 1, wherein the thickness of the reduced graphene oxide structure is between 20 nm to 5 μm.

7. A method for preparing an electrochemically activated and reduced graphene oxide structure, which comprises the following steps:

providing graphene oxide structure comprising a stack of layered graphene oxide flakes;

reducing the graphene oxide structure; and electrochemically activating the reduced graphene oxide structure in an electrolyte system, wherein electrochemically activating comprises at least partially sweeping cyclically an electrical potential around a potential equilibrium within a plurality of predetermined ranges.

8. The method for preparing an electrochemically activated and reduced graphene oxide structure according to claim 7, wherein the graphene oxide structure is reduced hydrothermally.

9. The method for preparing an electrochemically activated and reduced graphene oxide structure according to claim 7, wherein the plurality of predetermined ranges avoids Faradaic reactions.

10. The method for preparing an electrochemically activated and reduced graphene oxide structure according to claim 7, wherein electrochemically activating comprises charged ions permeating into the stack, thereby losing their solvation shell.

11. The method for preparing an electrochemically activated and reduced graphene oxide structure according to claim 7, wherein the plurality of predetermined ranges are consecutive, wherein each succeeding range is equal to or greater than its preceding range.

12. The method for preparing an electrochemically activated and reduced graphene oxide structure according to claim 7, wherein a number of sweeping cycles within each succeeding range is equal to or greater than the number of sweeping cycles within its preceding range of the plurality of predetermined ranges.

13. An electrode device for stimulation and/or recording of the central and/or peripheral nervous system, for neurostimulation and recording, wherein the electrode comprises the reduced graphene oxide structure according to claim 1.

14. The electrode device for stimulation and/or recording of the central and/or peripheral nervous system according to claim 13, wherein the reduced graphene oxide structure has a diameter of 25 μm or less and provides a charge injection limit from 2 $mC/cm^2$ to 10 $mC/cm^2$ and/or an impedance of 10 to 100 kΩ at a frequency of 1 kHz in an electrolyte system.

* * * * *